(12) United States Patent
John et al.

(10) Patent No.: US 7,747,318 B2
(45) Date of Patent: Jun. 29, 2010

(54) FUNCTIONAL FERRULE

(75) Inventors: Michael S. John, Larchmont, NY (US); Brett Wingeier, San Francisco, CA (US); Thomas K. Tcheng, Pleasant Hill, CA (US); Benjamin D. Pless, Atherton, CA (US)

(73) Assignee: NeuroPace, Inc., Mountain View, CA (US)

( * ) Notice: Subject to any disclaimer, the term of this patent is extended or adjusted under 35 U.S.C. 154(b) by 545 days.

(21) Appl. No.: 11/635,885

(22) Filed: Dec. 7, 2006

(65) Prior Publication Data
US 2008/0140149 A1   Jun. 12, 2008

(51) Int. Cl.
*A61N 1/00*    (2006.01)
(52) U.S. Cl. .......................................... 607/2
(58) Field of Classification Search ................ 607/2, 607/36, 86
See application file for complete search history.

(56) References Cited

U.S. PATENT DOCUMENTS

| | | | |
|---|---|---|---|
| 5,902,326 A * | 5/1999 | Lessar et al. ................... | 607/36 |
| 6,016,449 A | 1/2000 | Fischell et al. | |
| 6,033,431 A | 3/2000 | Segal | |
| 6,618,623 B1 | 9/2003 | Pless et al. | |
| 6,810,285 B2 | 10/2004 | Pless et al. | |
| 6,872,221 B2 | 3/2005 | Lytle | |
| 6,925,328 B2 | 8/2005 | Foster et al. | |
| 7,158,833 B2 | 1/2007 | Pless et al. | |
| 2004/0034368 A1 | 2/2004 | Pless et al. | |
| 2004/0073278 A1 | 4/2004 | Pachys | |
| 2005/0216072 A1 | 9/2005 | Mahadevan-Jansen | |
| 2005/0277912 A1 | 12/2005 | John | |
| 2006/0129204 A1 | 6/2006 | Pless et al. | |
| 2006/0155348 A1 | 7/2006 | de Charms | |
| 2006/0167531 A1 * | 7/2006 | Gertner et al. ................. | 607/86 |
| 2006/0173522 A1 | 8/2006 | Osorio | |
| 2006/0184210 A1 | 8/2006 | Singhal et al. | |
| 2006/0184220 A1 | 8/2006 | Singhal et al. | |
| 2006/0195156 A1 | 8/2006 | Singhal et al. | |
| 2006/0241717 A1 | 10/2006 | Whitehurst et al. | |
| 2006/0265022 A1 | 11/2006 | John et al. | |

OTHER PUBLICATIONS

Allegre, G., Avrillier, S., Albe-Fessard, D. (1994). "Stimulation in the rat of a nerve fiber bundle by a short UV pulse from an excimer laser," *Neuroscience Letters* 180: 261-264.

Bio-Chem Valve Inc. and Omnifit. (2003) "Standard Product Lines," located at <http://www.bio-chemvalve.com/products.asp>, last visited on Jun. 6, 2007. (1 page).

(Continued)

*Primary Examiner*—George Manuel

(57) ABSTRACT

Described here are intracranial ferrules, systems, and methods for sensing and stimulating neural tissues. The ferrules are generally designed to include a holding area for retaining an implantable device. In some variations, the ferrule itself may perform the sensing and stimulating functions. In other variations, the ferrule may function to sense data from neural tissues and the implantable device may function to stimulate neural tissues. In yet other variations, the ferrule may function to stimulate, and the implantable device may function to sense data from, the neural tissues. The sensing and stimulating functions may be used to detect and/or treat various neurological conditions.

61 Claims, 10 Drawing Sheets

OTHER PUBLICATIONS

Bio-Chem Valve Inc. and Omnifit. (2003) "Welcome to Bio-Chem Valve and Omnifit," located at <http://www.bio-chemvalve.com/>, last visited on Jun. 6, 2007. (1 page).

Burton, J.M., Peebles, G.A., Binder, D.K., Rothman, S.M., Smyth, M.D., (2005) "Transcortical Cooling Inhibits Hippocampal-kindled Seizures in the Rat," *Epilepsia* 46(12): 1881-1887.

Fork, R.L. (Mar. 5, 1971). "Laser Stimulation of Nerve Cells in Aplysia," *Science* 171: 907-908.

Imoto, H., Fujii, M., Uchiyama, J., Fujisawa, H., Nakano, K., Kunitsugu, I., Nomura, S., Saito, T., Suzuki, M. (Jan. 2006) "Use of a Peltier chip with a newly devised local brain-cooling system for neocortical seizures in the rat," *J. Neurosurg.* 104(1): 150-156.

Izzo, A.D., Richter, C.P., Jansen, E.D., Walsh, J.T. (2006) "Laser Stimulation of the Auditory Nerve," *Laser in Surgery and Medicine* 38(8): 745-753.

Safavi-Farokhi, Z., Bakhtiary, A. H. (2005). "The Effect of Infrared Laser on Sensory Radial Nerve Electrophysiological Parameters," *Electromyogr. Clini. Neurophysiol.* 45: 353-356.

Wells, J., Kao, C., Jansen, E.D., Konrad, P., Mahadevan-Jansen, A. (Nov./Dec. 2005). "Application of infrared light for in vivo neural stimulation," *Journal of Biomedical Optics* 10(6): 064003-1-064003-12.

Yenari, M.A., Zhao, H., Giffard, R.G., Sobel, R.A., Sapolsky, R.M., Steinberg, G.K. (2003) "Gene Therapy and Hypothermia for Stroke Treatment," *Ann. NY Acd. Sci.* 993: 54-68; 79-81.

\* cited by examiner

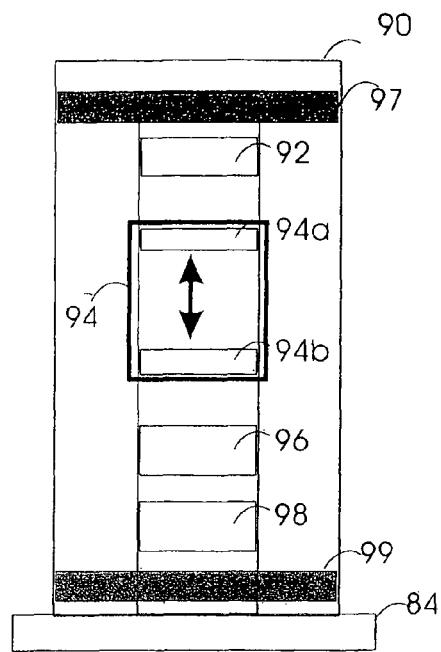
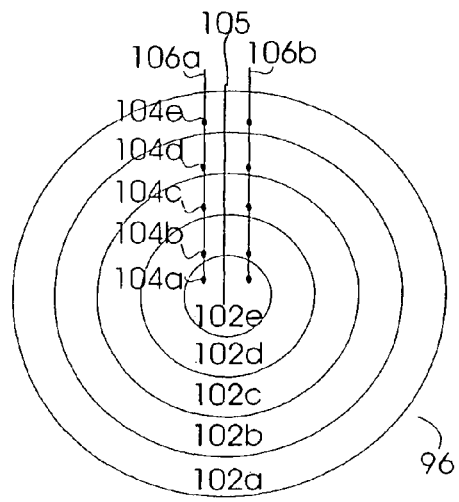
FIG.6A          FIG.6B
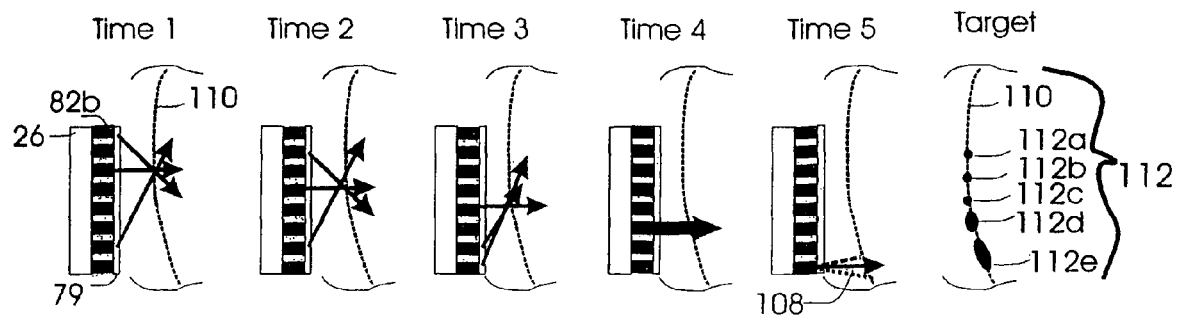
FIG.6C

FUNCTIONAL FERRULE

FIELD

The intracranial ferrules, systems, and methods described here relate to the field of neurology. More specifically, the intracranial ferrules, systems, and methods relate to the field of neural-directed sensing and stimulation.

BACKGROUND

Anchoring systems for securing medical devices within the cranium of a human patient have been previously described. Frequently, the device is a neurostimulator and the anchoring system is a ferrule which is affixed within the cranium in a region that has been surgically prepared by removal of a sufficient area of the skull. The ferrule is fastened to the skull using screws or an epoxy resin such as polymethylmethacrylate. The ferrule allows the neurostimulator to be situated within the cranium so that it is flush with, or slightly extruding above, the skull. Cranial placement is advantageous over implanting the neurostimulator in the body of the patient since shorter leads can be used which do not have to ascend along the neck, and which are therefore not prone to the same risk of breaking, kinking, or post-surgical migration from their intended position.

Known ferrules lack sensing and stimulating functionality, and are primarily designed for receiving and securing a neurostimulator within the skull. They may be shaped according to the individual contours of a patient's cranium and can be somewhat flexibly modified to adapt to the geometry of the surgically created region that is intended to receive the stimulation device. Cranial ferrules, when rigid, typically also provide the benefit of preventing the neurostimulator from insulting brain tissue as might occur due to an external force being applied to the device. Ferrules usually provide four or more points for securing attachment in order to minimize accidental dislocation of the device from the skull and one or more points for securing the device within the ferrule. Known ferrule devices also generally facilitate periodic removal and/or replacement of the device as may be required in order to replace a battery.

Accordingly, it would be desirable to have ferrules capable of sensing from neural tissues. It would also be desirable to have ferrules that are capable of stimulating neural tissues. Similarly, it would be desirable to have ferrules that employ their sensing and stimulating functions to detect and/or treat neurological conditions.

SUMMARY

Described here are intracranial ferrules, systems, and methods for performing various functions on neural tissues. For example, the ferrules may be employed to either sense data from neural tissues or stimulate neural tissues. In some instances, they are configured to both sense and stimulate. As used herein, the acronym "SEST" means "sensing and/or stimulation." The sensing or stimulation functions may be used to detect and/or treat a neurological condition. The neurological conditions that may be treated with the intracranial ferrules, systems, and methods described here include, but are not limited to, neurologically-mediated cardiac and cardiovascular disorders, headache disorders, inadequate cerebral perfusion, movement disorders, neurodegenerative disorders, pain, psychiatric and mood disorders, seizure disorders, spinal cord disorders, and voiding disorders.

The intracranial ferrules may sense data using a modulator that includes a sensing element, and may apply stimulation using a modulator that includes a stimulation element. The modulators may be configured as a grid on the dorsal or ventral surface of the ferrule and may include a combination of sensing and stimulating elements. The sensing element may include an optical sensor, an electrical sensor, a chemical sensor, a thermal sensor, a pressure sensor, a sonic sensor, or a combination thereof. In some variations, the data that is sensed from neural tissue includes, but is not limited to, EEG data, neuronal recordings (e.g., single neuron recordings, nerve potential recordings, local field potential recordings), ultrasound and doppler shift ultrasound data, oximetry data, optical sensing data, blood pressure recordings, impedance measurements, measurements of blood gases or chemical composition, measurements of temperature and acceleration, measurements of emitted or absorbed radiation (e.g., infrared spectroscopy measurements and spectrophotometric measurements), and combinations thereof.

When the modulator includes a stimulation element, the stimulation element may comprise an optical stimulator, an electrical stimulator, a chemical stimulator, a thermal stimulator, a pressure stimulator, a sonic stimulator, or combinations thereof. In some variations, the chemical stimulators deliver a therapeutic agent to the neural tissue to stimulate the neural tissue. Suitable therapeutic agents include calcium chelators, chemotherapeutic agents, cytokines, genetic therapy agents, immunotherapeutic agents, ion channel blockers, ion channel activators, neuropeptides, neuroregulators such as neuromodulators and neurotransmitters, nutrients, receptor agonists, receptor antagonists, photoreactive/electroactive compounds, and combinations thereof. In other variations, when thermal stimulators are employed, the thermal stimulators may either cool or heat the neural tissue.

The intracranial ferrules may also be designed with a number of convenience features. For example, the ferrule may include a portion that reversibly attaches to a power supply or include a portion that transmits power to an implantable device. Furthermore, the ferrule may comprise a conduit storage area for storing, connecting, organizing, and routing any leads or probes used with the ferrule.

The intracranial ferrules generally include a holding area for retaining an implantable device. The implantable device may be formed as a self-contained unit that is non-integral with the ferrule. An implantable device of this design may include one or more connectors on the ferrule for reversibly attaching the ferrule to the implantable device. At least one retainer tab may also be employed to reversibly secure the implantable device within the ferrule.

Also described here are systems for performing one or more functions on neural tissue. In some variations, the systems include an intracranial ferrule as previously described, and an implantable device. The implantable device may comprise a neurostimulator or a sensor. Accordingly, the implantable device may be used to sense data from neural tissue or stimulate neural tissue. In some variations, the implantable device is equipped to both sense and stimulate neural tissue. In other variations, the implantable device has a control subsystem that coordinates the sensing and stimulation functions of the ferrule. In yet other variations, the systems may include one or more probes for sensing and/or stimulation.

Methods for manipulating neural tissue are also described. In one variation, the method includes placing a ferrule having one or more modulators, as described above, within a portion of the cranium or a body tissue proximate the cranium, and sensing data from a neural tissue. The sensed data may be used to detect a neurological condition. In another variation, the method further includes stimulating a neural tissue. The stimulation may either increase or decrease the activity of the neural tissue, and may be provided to treat a neurological condition.

The intracranial ferrules may be placed within a portion of the cranium, a body tissue proximate the cranium, or any location within the skull. For example, when placed within a portion of the cranium, the ferrule may be situated within the periosteum or endosteum of the frontal, parietal, temporal, or occipital bones. In other variations, the ferrules may be placed within a body tissue or space proximate the cranium. For example, the body tissue may be the scalp or the meningeal membranes (dura mater, arachnoid mater, and pia mater). Examples of suitable spaces in which the ferrules may reside include subscalpular pockets, the subdural space, and the subarachnoid space.

The neural tissue that may be stimulated includes any tissue within the central nervous system. For example, portions of the brain (and the nerves within them), the meninges, and spinal cord tissue may be stimulated. In one variation, the cerebral cortex is the portion of the brain that is stimulated. The motor cortex, premotor cortex, and/or sensory cortex may also be particularly stimulated.

BRIEF DESCRIPTION OF THE DRAWINGS

FIGS. 6A-6C show schematic views of various optical transducers and a method of using the transducers.

DETAILED DESCRIPTION

Described here are intracranial ferrules, systems, and methods for performing one or more functions on neural tissue. The function may be sensing, stimulating, detecting a neurological condition, treating a neurological condition, or a combination thereof. The sensing and stimulating functions may be provided by the ferrule itself, or by a system that includes the ferrule and an implantable device such as a neurostimulator.

Figure 1:
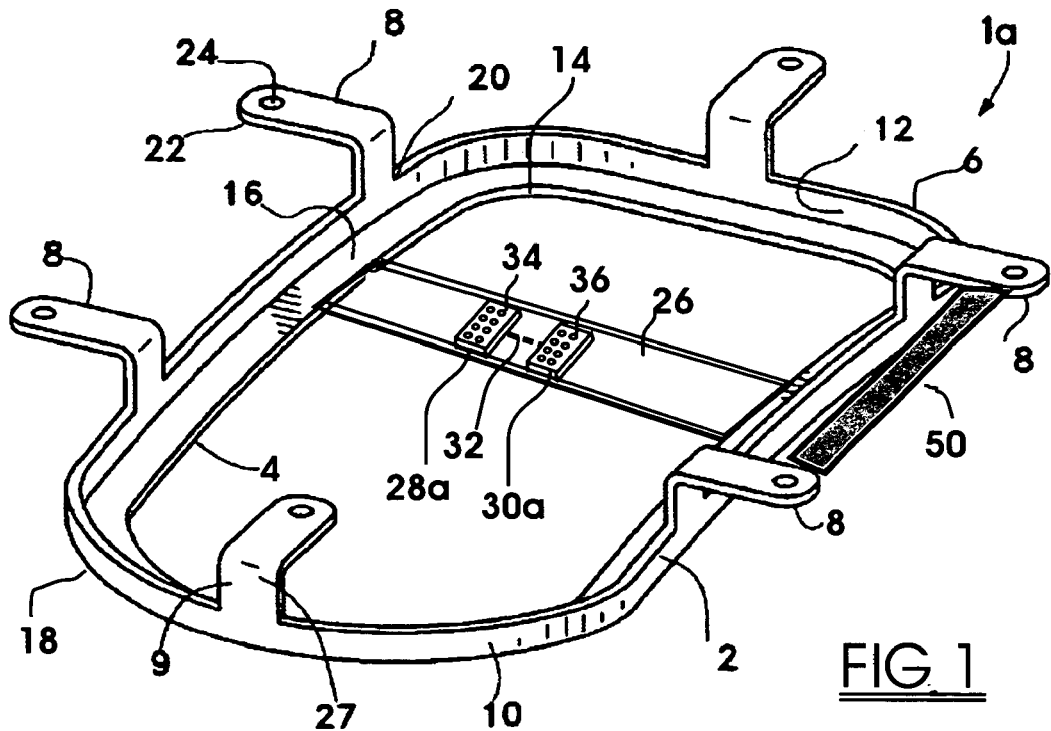
FIG. 1 shows a perspective view of an exemplary ferrule.
Figure 2:
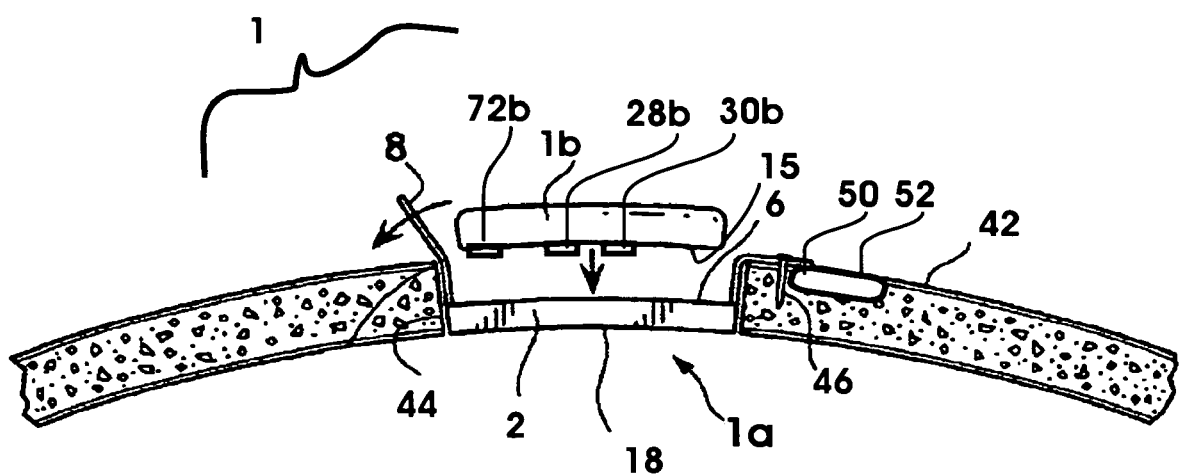
FIG. 2 shows a side cross-sectional view of the ferrule in FIG. 1 within the cranium and an implantable device prior to placement in the ferrule.

Turning now to FIGS. 1 and 2, ferrule 1a retains an implantable device 1b within a cranial opening of the patient, both of which work together to provide a ferrule system 1.

The ferrule 1a includes a wall portion 2, a shelf portion 4, a rim 6, at least one cranial attachment tab 8 for attaching the ferrule to the cranium, and a mechanism for removably securing the implantable device 1b within the ferrule 1a, such as a retainer tab 9.

The wall portion 2 encompasses and extends upwardly from the shelf portion 4. The wall portion 2 includes an outer surface 10 and an inner surface 12. The shelf portion 4 extends inwardly from the inner surface 12 of the wall portion 2 and defines an aperture 14. However, the aperture 14 need not be defined in the shelf portion 4. Alternatively, the aperture 14 may be at least partially replaced by a SEST-grid 26 or by various other probes (e.g., pressure or heat probes), or by a transparent plate (or grid) which may be coated on its ventral surface to deter accumulation of biological substrate, and which may be rigid or elastic. The shelf portion 4 may be any shape and may define one or a plurality of apertures. The shelf portion 4 includes a dorsal surface 16 and a ventral surface 18. The implantable device 1b may be secured between a dorsal surface of the shelf portion 4 and the retainer tab 9.

When the aperture 14 allows for the transmission of optical signals, the ventral surface 15 (shown in FIG. 2) of an implantable device may include an SEST-grid including optical SEST elements and the light can be transmitted from the implantable device, through the aperture 14, and to the brain of the patient. When the aperture 14 is simply empty space, the ventral surface 15 of the implantable device may include a SEST-grid having other types of SEST-elements such as electrical or thermal SEST-elements. The SEST-grid may exist on the ventral side of the ferrule, or on the ventral side of the implanted device, and can function equivalently as long as the ferrule is designed appropriately to enable the device to stimulate in its intended manner.

The rim 6 encompasses the wall portion 2 and is interrupted by the upwardly extending cranial attachment tabs 8. Each of the cranial tabs 8 includes a proximal end 20 and a distal end 22. The cranial attachment tab 8 is connected to the wall portion 2 relatively near the proximal end 20 and an aperture 24 for receiving a bone screw, or other connector, is defined relatively near the distal end 22. A retainer tab 9 for retaining an implantable device 1b is also shown in FIG. 1. The retainer tab 9 includes a detent portion 27 extending generally upwardly and inwardly from the wall potion 2. The implantable device 1b is retained within the ferrule 1a between the detent portion 27 and the shelf portion 4. Although only one detent portion 27 is shown, additional detent portions 27 may be incorporated that are within the scope of the invention, especially if the ferrule stores the device 1b and its power supply separately. The detent portions 27 may be bent into position prior to or upon insertion of the implantable device 1b. Also, the detent portion 27 may be utilized in combination with another retainer 9, such as with sutures to secure the implantable device 1b. Another fastening mechanism includes a screw which biases the implantable device 1b to remain secured within the ferrule 1a. For example, a screw may be used to tighten down a plastic tab (not shown) onto a dorsal surface of the implantable device 1b.

As shown, the ferrule system 1 includes at least one device-SEST interface, which allows the device to at least provide or control (e.g., route) SEST functions during treatment with the ferrule system 1. The device-SEST interface can include at least one of the following: a device-ferrule interface for providing communication between the device and the ferrule, a ferrule-SEST interface for providing communication between the ferrule and at least one SEST-element; a communication line for communication between at least one device-ferrule interface and at least one ferrule-SEST interface, and any other connections which are needed for the ferrule system to provide stimulation as intended. Two special types of device-SEST interfaces are a ferrule-conduit interface for providing communication between the ferrule and at least one SEST element of a conduit and a ferrule-grid interface for providing communication between the ferrule and at least one SEST element of a SEST-grid.

In line with this description, a device-grid interface is created when a ferrule system uses a device-ferrule interface that communicates with a ferrule-grid interface using a communication line. The device-grid interface allows the device to communicate with the SEST-grid. In one variation, this communication may be realized as a method having two steps. In the first step, the ferrule has a device-ferrule connector and communication occurs between the device and the ferrule. In the second step, a ferrule has a ferrule-grid connector and communication occurs between the ferrule and the grid. These two steps can occur approximately simultaneously or sequentially. In another variation, more than one type of device-ferrule connector or ferrule-grid connector may be used, and each type can be specialized to provide primarily one type of SEST-operation. For example, one type of interface connector can relate to communication involving SEST-control signals, while a latter interface connector can relate to communication of the SEST stimulation signals themselves. For example, when drugs are being delivered, two device-ferrule interfaces may be used, the first being a control interface for controlling flow of drugs, and the other being a signal interface for accepting fluids which are routed to the ferrule via the device.

A device-ferrule interface, which joins the ferrule 1a and stimulation device 1b, may be realized as a device-ferrule connector having a ferrule-side connection member (located on the ferrule) and a device-side member (located on the device) which can join together when the device 1b is inserted into the ferrule 1a. The ferrule-device interface can provide for transmission of signals between the device 1b, the ferrule 1a, and these can then be relayed to any SEST-elements which are used to provide treatment with a particular variation of the ferrule system control and communication signals, stimulation signals, and power. Examples of suitable device-ferrule connectors include, but are not limited to, zero insertion force (ZIF) connectors, low insertion force (LIF) sockets, sprung contacts, "punch down" blocks, insulation displacement connectors, plug and socket connectors, high density D-subminiature or D-sub connectors. In the case of chemical stimulation, one or more materials may be employed to form a substantially liquid tight seal for communicating a fluid stimulation signal from the device through the device-ferrule connectors to the stimulation conduit, including, but not limited to, silicone rubbers, metals, ceramics, polymers such as polyurethane, polyfluorocarbon, polyethylene, or polyvinyl chloride, and water-tight manifolds, with or without flanges, as further detailed at the website www.bio-chemvalve.com/.

The various types of interfaces described herein allow for communication to occur between the various components of the ferrule system 1. As used herein, the phrase "SEST communication" refers to sending and receiving "SEST-signals" which can include command, control, communication, sensing and stimulation signals as well as power signals which are used during the course of treatment. "SEST-probes" refer to components which implement sensing from, or stimulation of, anatomical targets. "SEST-elements" refer to elements on the probes, or on the SEST-grid, where sensing and stimulation occur. As used herein, the term "patterns" refers to temporal, spatial, and spatial-temporal patterns realized by sensing and stimulation functions.

Returning now to FIG. 1, the ferrule contains a SEST-grid 26 which contains device-grid interface connectors for communication between the SEST-grid 26 and the implantable device 1b. The dorsal side of the SEST-grid 26 may contain a control connector 28a for controlling functions of the SEST-grid 26. For example, if the SEST-grid 26 is designed for optical sensing and stimulation, the stimulator can send the control commands to the control connector 28a which then operates the circuitry of the SEST-grid to route optical SEST-signals related to specified SEST-elements (e.g., the SEST-elements are optical stimulators) using optical routing circuitry. The grid 26 also contains device-grid interface connector 30a, which can provide communication of optical signals, for example, optical stimulation signals, which are provided by the device 1b and relayed to different parts of the grid as dictated by the grid control connector 28a. Although the SEST signals can be relayed to the SEST-grid in a single fixed-manner, this variation allows for programmable stimulation to occur flexibly for any type of SEST modality. The grid control connector 28a can control circuitry in the device-grid interface connector 30a via a communication line 32 in order to route stimulation (or sensed) signals according to the stimulation (or sensing) protocol of the implantable device 1b. While control signals are communicated by single modularity I/O plugs 34, which in this case are electrical, and formed within the control connector 28a, the SEST signals which are communicated by I/O plugs 36, of the interface connector 30a, may be unique, and each may transmit optical, drug, electrical, or other SEST signals. The ferrule 1a may also include at least one heat sink tab 50, which can serve as a heat sink during cooling operations and which may be attached to other heat sink components as will be further described below.

Although not shown in the figures, it is noted that the ferrule 1a may be slightly elongated, and may contain a section for removably securing (e.g., with retainer tabs 9) a power source which has a connector for connecting the power source to the implantable device 1b. In this manner the power source can be independently removed from the ferrule 1a, without replacement of the implantable device 1b. Further, the elongation can serve to provide distance between the battery power source and the heat sink tab, and other areas of the ferrule system 1 which may become warm during stimulation treatment. Further, although the ferrule here is shown as a rigid structure, it may also be realized partially or fully as a soft/elastic, biologically inert and compatible material which may contain approximately transparent regions. Additionally, the implantable device does not have to provide stimulation and can also be a device such as that which wholly or primarily senses and stores sensed data, senses data and provides alert signals when certain conditions are detected, or, which otherwise provides a therapeutic benefit. The device may operate with or without implanted SEST conduits, with or without a SEST-grid, and may utilize SEST probes located within the head and neck, above, within, or under the skull, dura, and cortex, as well as in other locations of the patient's head and body. Lastly, the SEST-grid does not have to be located directly upon the ventral side of the ferrule, but can alternatively be biased and extend towards the cortex. This may occur using an elastic material which performs such biasing, such as a flexible, coated spring device. Further, components which may be realized on the ventral side of the ferrule can also exist on the ventral side of the implantable device, as long as the ferrule is configured to enable these components to function in their intended manner. For example, the SEST-grid can be implemented on ventral side 15 of the implantable device 1b, but only if the ferrule 1a is designed to permit SEST signals to be transmitted between the device 1b and the cortex of the patient. Other modifications are also possible for the ferrule 1a of the ferrule system 1 without departing from the spirit of the invention.

As shown in FIG. 2, the patient's cranium 42 is surgically altered to provide a cranial opening 44, and the ferrule 1a is surgically positioned within the opening 44 and attached to the cranium 42. When the ferrule 1a is formed of pliant material, the attachment tabs 8 are capable of being bent over an edge of the cranial opening 44 as shown while the ridge 6 can be designed to provide the necessary structural rigidity for device support. After the attachment tabs 8 are bent into position, the ferrule 1a is secured to the patient's cranium 42 with bone screws 46. A heat sink 52 may also be implanted in the patient's cranium 42 in order to conduct heat away from the ferrule transferred by the heat sink tab 50 which may be implemented as part of the ferrule 1a or the implantable device 1b. In the variation of the ferrule system 1 which is shown, the device 1b contains interface connectors 28b and 30b which plug into interface connectors 28a and 30a of the SEST-grid 26 to create device-grid interfaces.

If the area in which stimulation is desired is large, or is not known exactly, it may be advantageous to implant more conduits (i.e., leads for electrical, optical, chemical, or other stimulation) than can be connected to the implantable device at one time. This allows later adjustment of the stimulation target by swapping conduits in a simple surgical procedure. It may be important to be able to locate the proximal end of each extra conduit after many months or years of implantation. It may also be important to be able to unambiguously identify each extra conduit, by examination of the proximal end, in order to select conduits for device connection.

Figure 10:
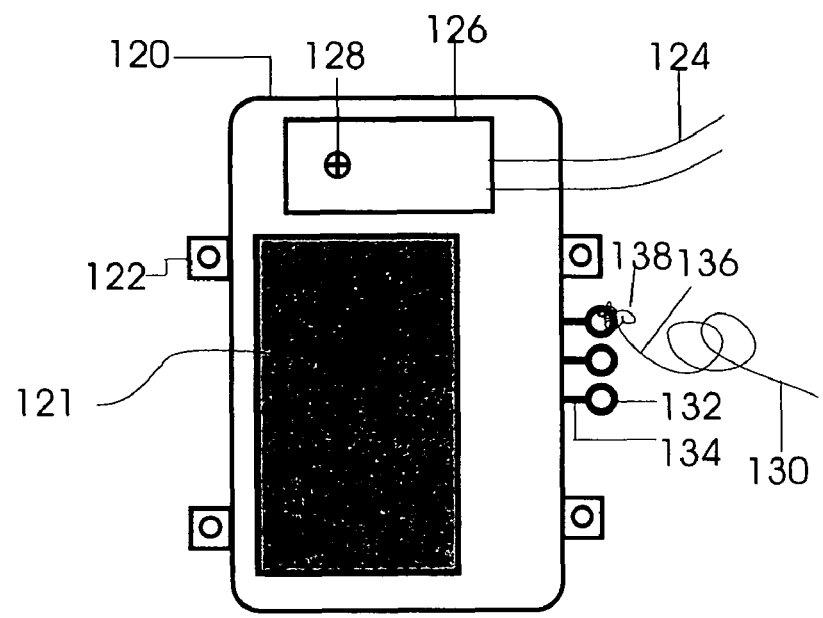
FIG. 10 is a perspective view of a conduit attachment mechanism.
Figure 11:
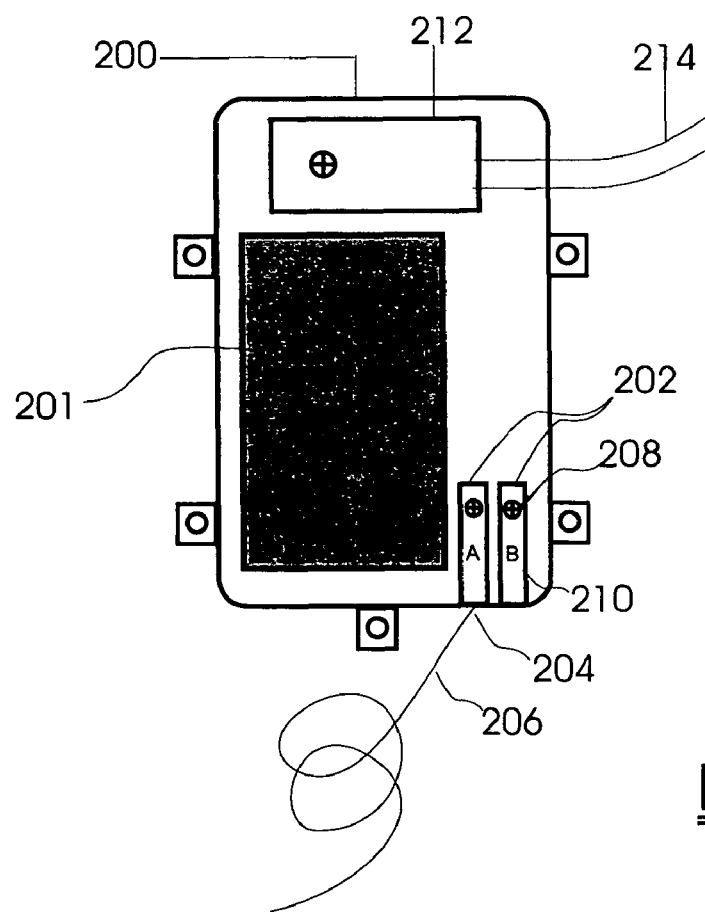
FIG. 11 shows a perspective view of another conduit attachment mechanism.

To this end, attachment points may be provided on the ferrule. FIGS. 10-11 illustrate variations of such attachment points. In FIG. 10, ferrule 120 is affixed to the skull using tabs 122. One or more active conduits 124 are connected and secured to the ferrule using cover 126 and screw 128. The exact mechanism of attachment for active conduits 124 is not essential; these conduits may also be connected to the implantable device 121 itself, or connected to the ferrule 120 in other ways.

One or more inactive conduits 130 are implanted but not used at this point. In FIG. 10, a set of one or more attachment points 132 is provided on the ferrule 120. Each attachment point is provided with a visible label 134 that may be noted in surgical records and/or used to visually identify the inactive conduits during a later surgical procedure. The proximal end 136 of each inactive conduit 130 may be tied with one or more sutures 138 or otherwise attached, for example, using commonly available surgical supplies to an attachment point 132.

Another variation of how conduits may be attached to a ferrule is shown in FIG. 11. In FIG. 11, a set of one or more attachment points 202, consisting of a protective sleeve into which the proximal end 204 of an inactive conduit 206 may be inserted, is provided on the ferrule 200. Each inactive conduit 206 is secured at an attachment point 202 using a screw or other tightening mechanism 208. Each attachment point is provided with a visible label 210 that may be noted in surgical records and/or used to visually identify the inactive conduits during a later surgical procedure. The mechanical interface between each attachment point 202 and each proximal end 204 of inactive conduit 206 may approximately or exactly resemble the mechanical interface between the cover 212 and one or more active conduits 214. As mentioned above, the exact mechanism of attachment for active conduits 214 is not essential; these conduits may also be connected to the implantable device 201 itself, or connected to the ferrule 200 in other ways.

Figure 12:
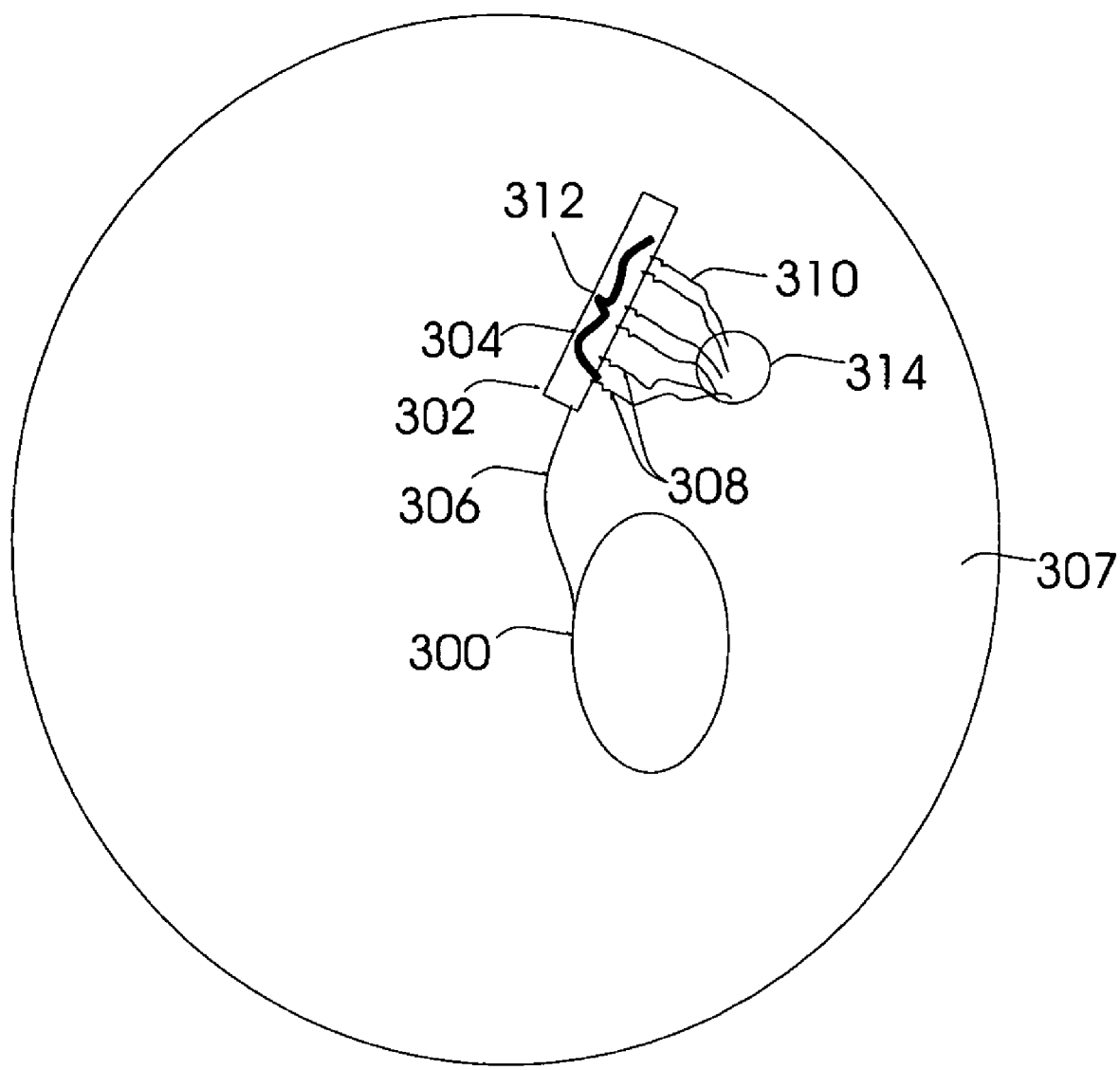
FIG. 12 shows a perspective view of a conduit attachment mechanism that includes a skull mounted connector.

A further conduit connection system is shown in FIG. 12. As shown in FIG. 12, the ferrule 300 (or ferrule/implantable device combination) is connected to a first area 302 of the skull mounted connector 304 via connector conduit 306. The skull mounted connector 304 may be affixed to the surface of the skull 307 or embedded within the skull 307. The skull mounted connector 304 may also reversibly couple to one or more proximal ends 308 of tissue conduits 310 at a second area 312 in a manner that allows the skull mounted connector 304 to relay signals to or from neural tissue. In FIG. 12, the proximal ends 308 of the tissue conduits 310 traverse a burr hole 314 to attach to the skull mounted connector 304. The skull mounted connector 304 may be configured to reversibly couple to any type of tissue conduit 310, e.g., electrical, chemical, thermal, etc. The connector conduit 306 is configured to relay signals, e.g., relay stimulation signals to the skull mounted connector 304, or relay sensed data from the skull mounted connector 304. Other components may be added to the conduit connection system as desired to aid signal relay between neural tissue and the skull mounted connector 304, and between the skull mounted connector 304 and the ferrule 300. For instance, a multiplexor circuit that controls the number of conduits utilized, and/or which selects particular conduits for use may be included in the skull mounted connector 304.

Ferrule-Mediated Sensing and Stimulation

As described, both sensors and stimulators may be attached directly to the ferrule rather than to the implantable device, so that explanation and implantation of the implantable device does not require the extra time and effort and risk (e.g., inadvertent tugging, cutting, or breakage) associated with disconnection or reconnection. Instead, the implantable device may be "snapped" in and out of the ferrule, while communication between the device 1b and the other components of the system 1 may be achieved using at least one ferrule system interface connection (e.g., interface connector 30a).

In some variations, a conduit storage area for providing at least one of storing, organizing, connecting, and routing of conduits, including residual extra length of conduits, which normally exist after implantation. In known techniques, after the distal sections of the conduit are implanted and the proximal sections are attached to an implantable device, any extra length is normally wound up and stored under the scalp using conduit anchors and/or a pouch-type of holder. This practice is often disadvantageous because the extra length may cause unnecessary irritation to the patient, or during replacement, the extra length increases the risk that a surgeon may unintentionally and/or unknowingly sever a conduit or induce conduit migration. Furthermore, wound-up conduits may be difficult to identify post-procedure (e.g., lead 1 might be confused for lead 4). The provision of a conduit storage area located in the ferrule therefore provides additional advantages to the ferrule used by the ferrule system.

Figure 3:
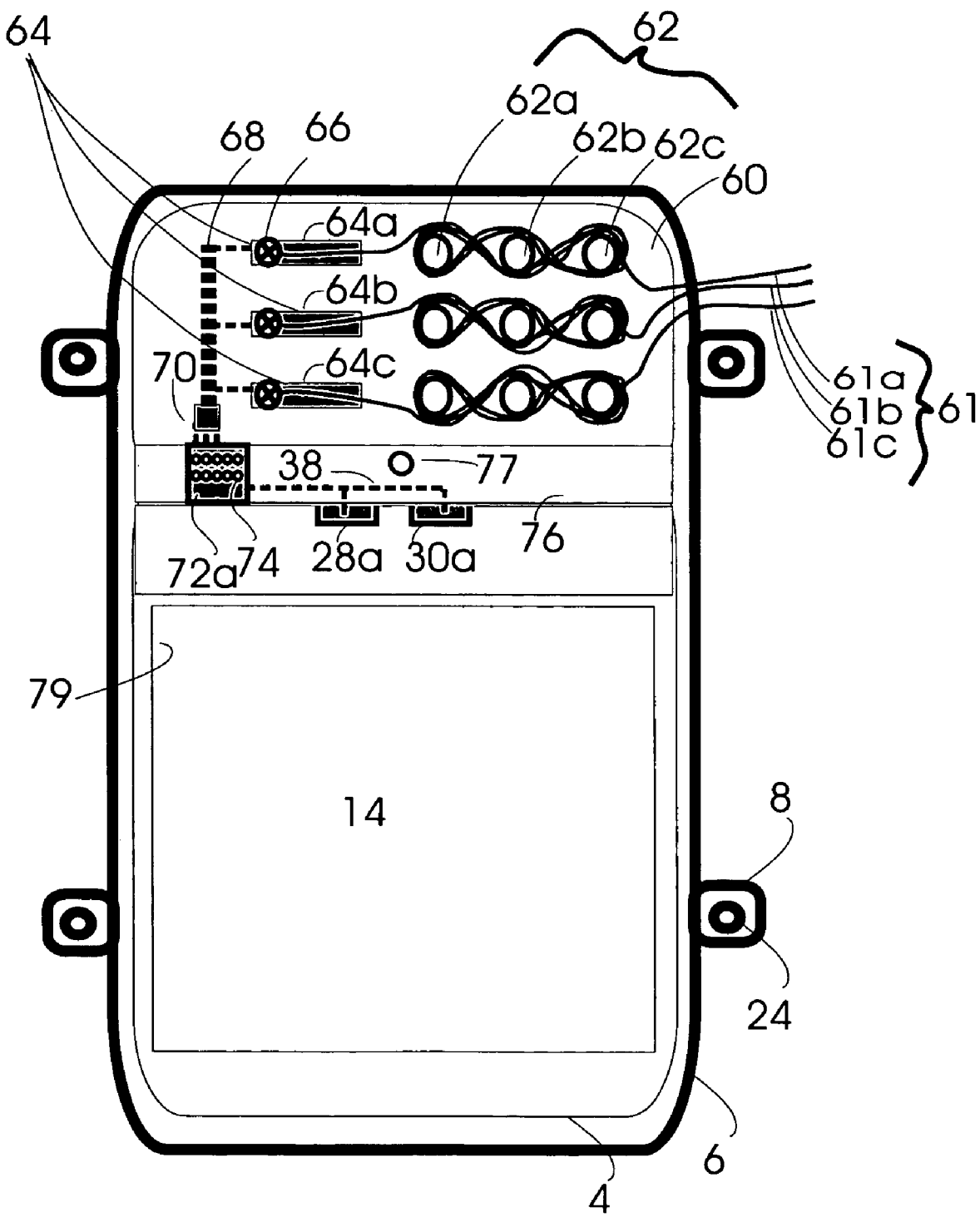
FIG. 3 is a top view of a ferrule having a conduit storage area.

Moving now to FIG. 3, the ferrule system 1 is shown having a SEST conduit storage area 60 for storing a SEST conduits 61. The storage area 60 may provide storage, routing, and connection of the conduit to the implantable device 1b, ferrule 1a, or other components of the ferrule system 1. For example, SEST signals sent by the implantable device 1b may be routed to the SEST conduits 61 to implement programmable SEST functions as dictated by a treatment program. In the variation illustrated in FIG. 3, three SEST conduits 61*a*, 61*b*, and 61*c*, are shown. One of the conduits 61*a* is wrapped around three conduit anchors 62*a*, 62*b*, 62*c* and then extends into a conduit connection member 64*a* where it may be secured by a connection apparatus 66. The conduit connection members 64 can be configured to route the SEST signals along a relay pathway system 68 to (and from) their intended targets such as the implantable device 1*b*, ferrule 1*a*, or grid 26. Also shown is an aperture 14 formed into the shelf 4. The aperture may be an empty space, may contain a SEST probe, or may contain an interface plate 79 which can be an optically transparent surface which may be removably attached to the shelf 4, and which may fit between the shelf and device. This type of configuration permits an optical SEST-grid to be located on the ventral surface of an implantable device and to perform a function on neural tissue.

As is shown in FIG. 3, a pathway controller 70 can dynamically route the SEST signals according control signals sent to it by the therapy program. Alternatively, the relay pathway system 68 can be fixed and only permit the SEST signals to be communicated between the conduits and the other components of the ferrule system 1, in a pre-defined and unchanging manner. The pathway controller 70 can be controlled by signals sent by the device 1*b* via a device-SEST interface 72 which is realized here as a ferrule side interface connector 72*a* and a stimulator side interface connector (e.g., as shown in FIG. 2 as element 72*b*). The device-SEST interface not only allows for communication of SEST control signals between the device and the pathway controller 70, but also SEST stimulation and sensing signals which allow SEST functions such as sending stimulation signals and receiving sensed data. Accordingly, similar to the SEST-grid connectors 28*a*, 30*a* the ferrule side interface connector 72*a* can contain multiple plugs 74, each of which may be used for unique SEST operations. For example, one plug can transmit electrical signals while another plug transmits optical signals, electrical power, or drug, when the device 1*b* provides drug therapy. The ferrule side connector 72*a* may alternatively, or additionally, transmit SEST signals to the SEST-grid controller connector 28*a* and/or SEST-grid stimulation connector 30*a* via communication line 38 which is located upon the storage area shelf 76 and in which the ferrule side connector 72*a* may be formed. Rather than the communication line 38, a second relay pathway system (not shown) may be used which can communicate signals between the interface connector 72*a* and the pathway controller 70. Further, rather than components 42, 24, 66, 68, 70 and 72, which serve as a particular variation of a device-SEST interface, this may occur using a single connector, with a single plug, located on the ferrule which has a device-ferrule connector for allowing rapid connection of the device 1*b*, and a ferrule-SEST connector which allows for permanent or temporary connection of one or more SEST conduits. In one variation, the relay pathway 68 consists of three independently isolated electrically conductive wires which lead to a pathway controller 70 that is a programmable multiplexor which is controlled by SEST control signals provided by the stimulator 1*b* through at least one plug of the device SEST interface 72, and where other plugs transmit the electrical sensing and stimulation signals.

In one variation, the SEST conduits 61 are electrode leads each having at least one contact, and distal ends of the leads are implanted in a subject. The proximal ends of the leads are wrapped around the conduit anchors 62. It is noteworthy that by wrapping the leads in an alternating clockwise/counterclockwise fashion, the effects of externally applied magnetic fields are attenuated since the induced current will be oriented oppositely along different lengths of the conduits. The leads are then inserted into the conduit connector 64, which in this case is an insulated sheath at the end of which is a conductive screw 66 used for keeping the proximal end of the conduit in place.

In another variation, the SEST conduits 61 are optical fibers each having at least one distal tip which is implanted so that the optical signal is emitted into target neural tissue. The proximal ends of the fibers are wrapped around the conduit anchors 62 and are then inserted into the conduit connectors 64, which in this case may be optical connection junctions at the end of which are screws 66 used for keeping the proximal ends of the fibers in place. In this variation, the pathway system 68 consists of 3 optical fibers which lead to a pathway controller 70 which is a programmable optical router which is controlled by control signals sent from the stimulator 1*b* through at least one plug 74 of the connector 72*a*, and where other plugs transmit other types of SEST signals. When the SEST functions include both electrical and optical implementations the components of the conduit storage area 60 may be adapted as a hybrid of the two variations just described. In yet another variation the ferrule-conduit interface is implemented within the conduit storage area 60.

Figure 4:
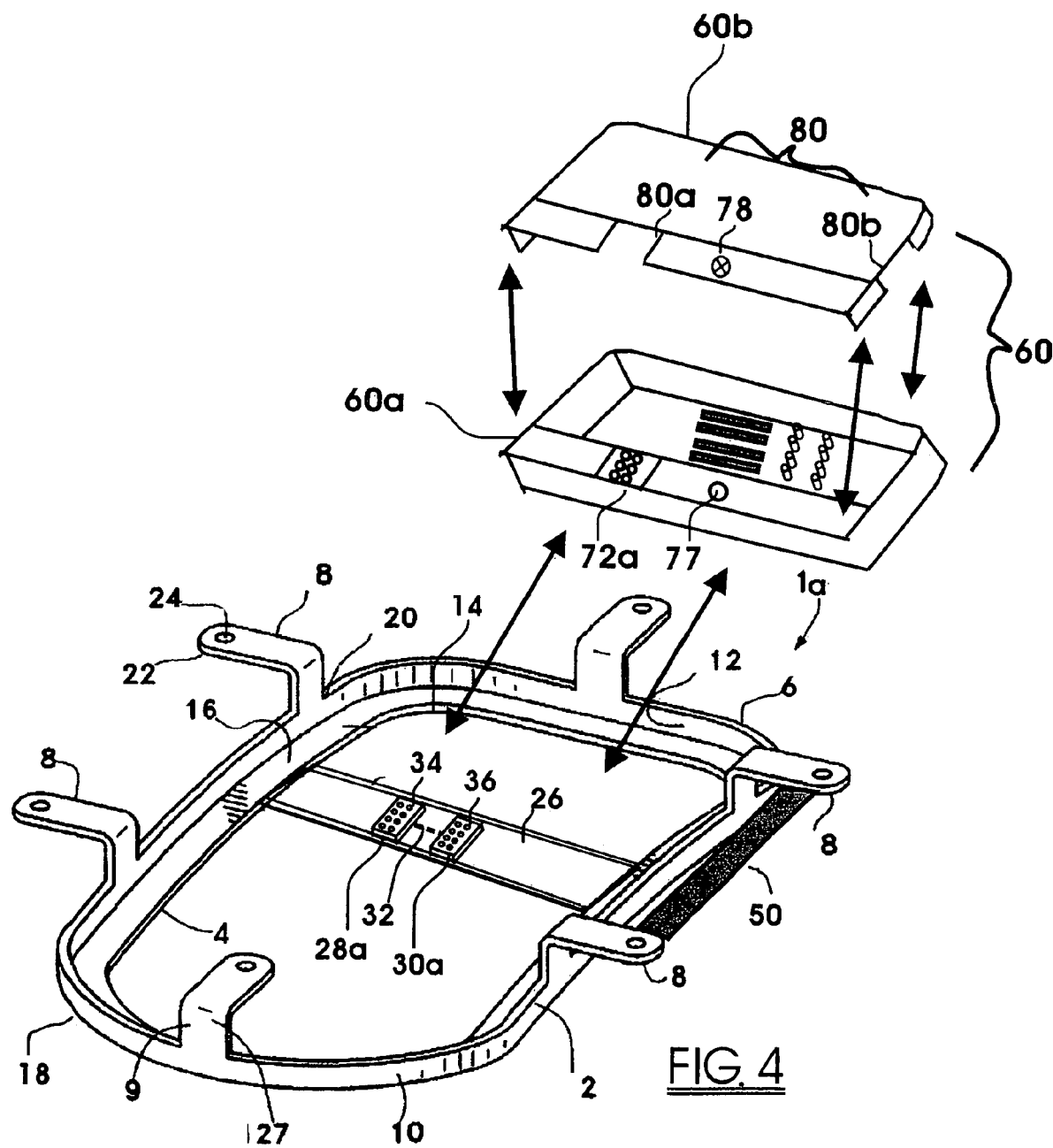
FIG. 4 shows an expanded view of another conduit storage area.

FIG. 4 shows the conduit storage area 60 and the ferrule 1*a* in an expanded view. In this variation, the base 60*a* of the storage area 60 can be removably affixed to the ferrule 1*a* by using additional detention members, screws, or other types of fasteners. Alternatively, the base 60*a* can be formed within the ferrule 1*a* so as to permanently reside therein and may be glued to the shelf 4 of the ferrule 1*a*. The storage area 60 has a cover 60*b* which can be secured to the base 60*a* at time of implant, using a securing mechanism such as one or more screws 78 which are accepted by appropriately spaced threaded holes 77 in the base 60*a*. The cover 60*b* can have several slits 80, such as a connection slit 80*a* which enables interface connectors to join together, and a conduit slit 80*b* which allows for the routing of conduits when traveling from inside the storage area to the patient or other device. The slits 80, as well as other portions of the base cover 60*b* may contain elastic deformations (e.g., rubber), covers, and caps or can be sealed with an epoxy resin or biocompatible silicon in order to provide a water resistant seal when the base and cover are attached so that the storage area is resistant to fluid leakage. The storage area 60 may also have a breach sensor in order to detect fluid leakage. When the ferrule system 1 contains a SEST-grid, the connector 72*a* may not only provide for SEST communication between the device 1*b* and any conduits, but also between the device 1*b* or conduits and the SEST-grid connectors 28*a*, 30*a* of the SEST-grid 26.

Although FIG. 4 shows an enclosed conduit storage area, other storage area designs may be used. For example, the conduit storage area may be configured as a non-enclosed shelf. Alternatively, the storage area may be filled with a silicone or other polymer gel, which subsequently hardens to produce a clear, waterproof matrix within which the conduits are affixed.

The conduit storage area enables a number of novel features of the ferrule system 1. For example, the storage area allows for easy replacement of the implantable device when used with complex system designs that rely upon stimulation sources located outside of the housing of the ferrule system 1. In one variation, when the ferrule system provides optical stimulation, the conduit 61*a* can serve as an input conduit wherein a light signal provided by an extracranial light source, such as an implanted laser device, is received by the ferrule system and is routed to the pathway controller 70 along a pathway system 68 consisting, at least in part, of optical fibers. The implantable device 1*b* routes the light by sending control signals to the pathway controller 70, which in this case is a programmable optical router/diverter, in order to (programmably) deliver optical signals through output conduits 61b and 61c. In another variation, when the ferrule system provides chemical stimulation, the conduit 61a, can serve as an input conduit wherein a drug provided by an extra-cranially located drug pump, such as an implanted drug pump, is received by the ferrule system and is routed to the path controller 70 along a path system 68 which includes catheters. The implantable device guides the drug using the path controller 70, which in this case may be a programmable valve assembly, in order to deliver one or more types of drug through output conduits 61b and 61c. Rather than delivering drug through the conduits 61b, 61c, the drug can be routed to elements of the SEST-grid 26, which may be configured to provide chemical therapy. In this variation, the device 1b retained by the ferrule 1a of the ferrule system 1 helps to provide therapy by functioning as a signal router for the stimulation (and sensing) signals, as there is no need to have direct connections between the device and the SEST-conduits.

Figure 5:
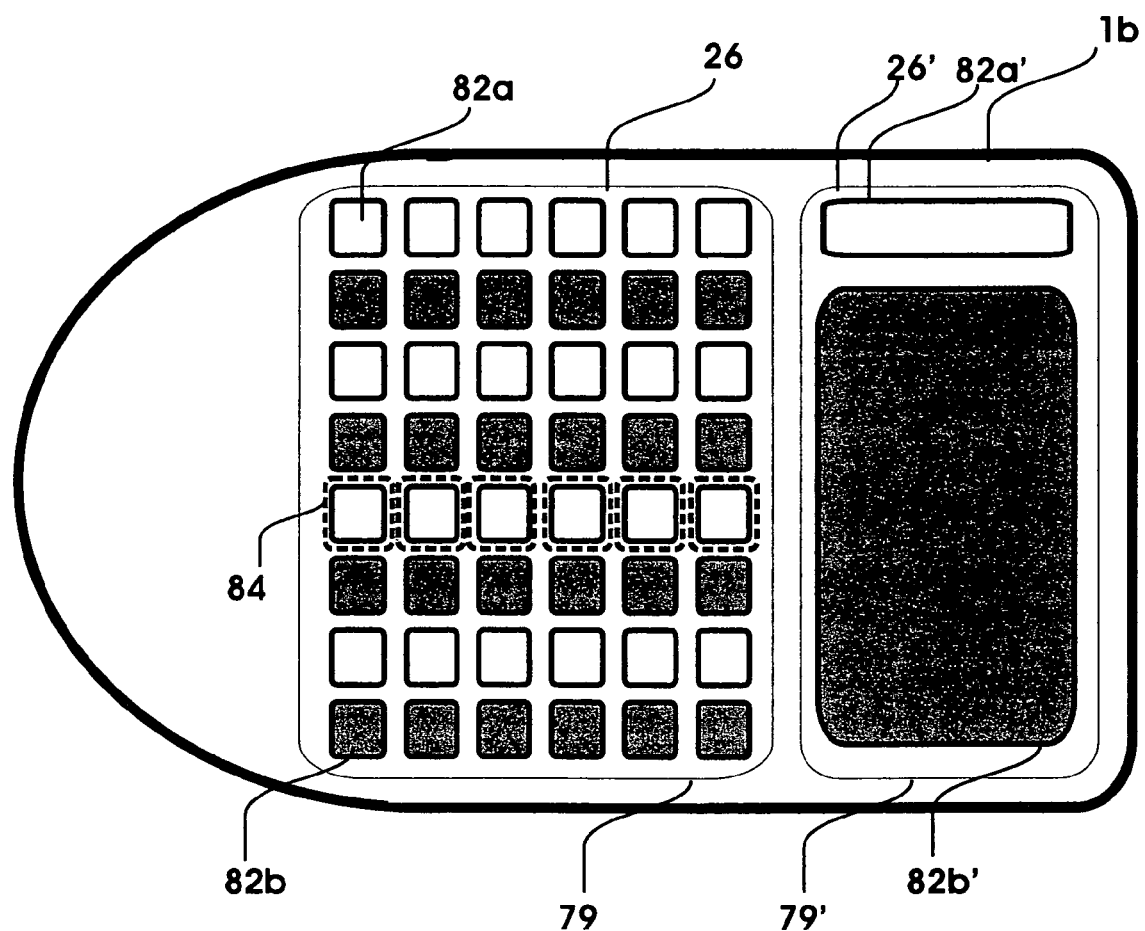
FIG. 5 shows a schematic view of a ferrule having a plurality of sensors and stimulators arranged on a grid. The sensors and stimulators are on the ventral surface of the ferrule.

FIG. 5 shows a variation of the ferrule system having a ventral surface configured with two SEST-grids 26, 26' which permit two modalities of stimulation. For example, the first SEST-grid 26 may permit the implementation of spatial patterns of stimulation using a grid of both sensing elements 82a and stimulation elements 82b. The SEST grids 26, 26' can be provided within the ferrule 1a, or can exist on the ventral surface 15 of the implantable device itself when the ferrule 1a contains an aperture 14 into which the SEST-grid of the implantable device is inserted. For example, the stimulation elements 82b may provide optical stimulation, and the sensing elements 82a may provide optical sensing. In another variation, when the elements are electrical, the elements may provide electrical sensing and stimulation. The SEST-grid 26 may also provide thermal, vibrotactile, impedance, pressure, sonic, and chemical sensing and stimulation elements. Thus, second SEST-grid 26' may provide sensing from sensing element 82a' and stimulation from stimulation element 82b' that differs from sensing and stimulation provided by elements 82a and 82b, respectively.

The ventral surface 15 of the stimulation device 1b may contain a SEST-grid 26 configured to implement stimulation patterns in two modalities, or may contain two SEST-grids 26 and 26' as described above. In the latter case, the ferrule may contain two apertures, the first having an interface plate 79 with a first set of characteristics (e.g., transparent) and the second aperture 14' being simply a space or having an interface plate 79' which has a second set of characteristics (e.g., efficient heat transfer). The interface plates may be replaced without removing the entire ferrule, for example, by removing two or more securing screws which secure the plates to the ventral surface 15 of the implantable device or dorsal surface 16 of the shelf portion 4 of the ferrule 1a.

Sensing and Stimulation Grids

The SEST-grid may be designed to provide a number of different kinds of sensing and stimulating functions. The SEST-grid may contain at least one stimulation element or sensing element, and in some instances, may include two or more sensing or stimulation elements.

When the SEST functions are electrical, the grid elements 82 can be electrical sensors 82a and stimulators 82b. The stimulation elements 82b are independently operated to provide arbitrary waveforms of stimulation and each element can serve to provide monopolar or bipolar stimulation, and may be a ground contact or may be floating. When the grid 26 is sufficiently adjacent to the cortex, the sensing elements 82a can sense brain activity including the local electrical fields generated by the compound action potentials of underlying cortical populations. The stimulation elements 82b of the grid 26 can also provide stimulation in conjunction with SEST-elements located on probes which are implanted in the brain at more distal locations (e.g., depth electrodes having contacts implanted intra-cortically or at subcortical locations). When the SEST functions are electrical, the interface plate 79 may not be included or may be designed to allow electrical conductivity between the brain and the SEST-grid 26.

When the SEST functions are chemical, the grid elements 82b are designed to release one or more drugs according to the stimulation program. The elements 82b may be configured with valves in order to regulate the flow of therapeutic fluids during dispensing operations. The SEST-grid elements 82a may include various types of chemical sensors (e.g., biochips) as are known in the art.

When the SEST functions are thermal, the stimulation elements 82b may be designed to provide cooling or heating of adjacent brain tissue. When cooling, element 82b may be connected directly or indirectly to a heat sink of the ferrule system 1. The ferrule system 1 may work with a reservoir system to remove heat to a distal location which may have a reservoir, which may also be cooled. The sensing elements 82a may be chemically or electrically based thermometers or other types of thermo-sensitive devices from which temperature can be determined.

When the SEST functions are vibrotactile, the stimulation elements may be a vibration motor, a sonic transducer (e.g., a speaker), or other type of pressure transducer. The stimulation element 82b may contain an elastic deformable membrane which can "push" outward or "pull" inward to increase or decrease intracranial pressure in a quick (e.g., 100 msec) or slow (e.g., one minute) manner. The pressure transducer 82 may be mechanical (e.g., an electrically controlled diaphragm), or electro-chemical (e.g., an electro-active polymer that changes volume, such as an electrorheological fluids coupled with the elastic response of polymeric gels). Sonic transducers may also be used to emit and record sound.

When the SEST functions are related to the measuring of impedance, the elements 82 may be electrical and the SEST-grid 26 may relay the sensed data to the implantable device for performing both impedance plethysmography and the subsequent derivation of impedance tomography in order to ascertain either spatial or spatio-temporal patterns of impedance as measured by different elements 82 over time (e.g., as may be related to blood flow patterns).

When the SEST functions are optical, the light sources may be provided in the grid 26 itself (e.g., a laser diode). Additionally, the optical signals may be generated by the device 1b or at an external location (e.g., an implanted or externally located laser device), and the signals can be routed to the designated elements 82 in the SEST-grid 26. Optical sensors, sensing, and processing methods may be used, for example, in determining such measures as cerebral perfusion as described in co-pending U.S. application Ser. No. 11/404, 579. Optical SEST-elements 82 can include sensors of visible, ultraviolet, near infrared wavelengths, or other wavelengths and may utilize spectroscopy (e.g., near-infrared spectroscopy or NIRS) in the analysis of the optically sensed data.

The interface plate 79 may be utilized to provide a barrier between the SEST-grid 26 and the neural tissue. When the stimulation is optical, a substantially transparent interface plate 79 can be provided in the aperture 14 of the ferrule in order to isolate the SEST-grid 26 from the biological fluid and tissue of the brain. The interface plate 79 may be coated so as to prevent adhesion of biological materials or other obstructions to the light path. The interface plate may also be realized as a molded assemblage of focusing lenses. Alternatively, rather than being composed of substantially transparent material, the interface window may be constructed or coated with a material which filters light within, or outside of a specified band. A section of the interface window may also be layered with more than one film, each of which is capable of passing or stopping light within a specified range, as it is emitted or sensed by optical SEST elements. For example, films may be used to filter light so that only one or more bands of certain frequencies that are used to detect oxygen utilization in tissue are passed.

The interface plate 79 may simply be a clear glass or plastic plate, or may be formed into a grid of pixels 84. Further, the interface plate 79' may be a layered plate with electronically operable components formed into the pixels 84. For example, the pixels 84 may be configured with programmable routers, apertures, shutters, lenses, or polarizers (e.g., electroresponsive polarizing film) in order to adjust the amount, duration, direction, and other characteristics of light which passes through any of the pixels 84. If the stimulation includes electrical stimulation, the pixels 84 may each be conductive surfaces which are surrounded by non-conductive material. If the stimulation includes drug delivery, then the pixels 84 can contain programmable valves. The pixels 84 of the interface grid 79' can be controlled by the same circuitry that controls the SEST-grid, or may have their own control mechanism.

The ferrule system 1 can be used for drug delivery using SEST conduits (which function as input and output catheters) and/or the SEST-grid. If a SEST-grid element is configured for drug delivery, the drug may be provided either by the device 1b itself, or by another drug pump which works with the device and which sends drug to the device using one of the SEST conduits 61. In these variations the ferrule system 1 operates as either a pump and/or routing device which contains a drug reservoir, or alternatively controls the routing and delivery of drug located in a distal pump. The ferrule system may also use its SEST conduits for shunting fluid in an active or passive manner. If passive, then the ferrule system may simply open a valve to allow the flow of fluid through a grid element 82, or a SEST conduit (e.g., an "input" catheter), so that it is relayed to a different location, for example, using a different SEST conduit (e.g., an "output" catheter) or a skull mounted shunting device which may contain a flow controller (e.g., a valve) or pressure sensor, so that fluid is removed to a location outside of the cranium.

Turning now to FIGS. 6A-C, various stimulation elements and methods of using these elements are shown with respect to providing optical stimulation, although a portion of these may also be adapted to be used with other types of stimulation. In FIG. 6A an exemplary variation of an optical stimulation element 90 is shown having a light emitter 92 which may be a locally realized light source, such as a diode, or which may be a distally realized light source, which transmits light from a different location through the implantable device (e.g., a neurostimulator) 1b to be emitted from the emitter 92. The light is transmitted from the emitter 92 through a lens portion 94 having an upper lens 94a and a lower lens 94b, each of which may be concave (e.g., bi-concave) or convex and which may be positioned to cause a broadening or narrowing of light (e.g., focal dispersion) in a predefined manner. Alternatively, the optical stimulation element 90 may be provided with a lens portion 94 which permits the adjustment of the distance between the upper 94a and lower lens 94b. The light may then be transmitted through an aperture 96 designed to create a stimulation field area as required to provide intended stimulation of the neural target. In one variation, similar to the lens portion 94, the aperture 96 may be programmably adjusted, and may have a fully closed position wherein it serves as a shutter in order to completely block the light beam. Such a shutter feature may be useful when light sources are used that are incapable of rapidly transitioning from an off-to-on state, so as to be able to provide a stimulation pulse in patterns that may be called for by the therapeutic protocol. For example, although lasers can emit continuous laser pulses, these often can not be started and stopped in a manner required by optical stimulation therapy. Accordingly, a shutter or diverter may be useful in selecting one or more single pulses from the pulse train, thereby permitting shaping of the envelope of the optical signal. For accurate timing, the shutter may be controlled by additionally sending trigger pulses from the laser to the control subsystem of the device 1b.

Next, the light encounters a diverter 98 which may be realized as another lens, or a mirror which causes the light to first encounter a pixel 84 of the interface plate 79', and subsequently neural tissue, at a desired angle. The diverters 98 of two or more optical elements 90 may be angled prior to implantation so that their emitted beams produce a pattern on tissue located a specified distance from the stimulation elements. Accordingly, an optical SEST-grid 26 is well suited to provide both two and three dimensional optical stimulation patterns. In one variation, the neural tissue structure and other properties are assessed by an MRI procedure (e.g., DTI) in order to derive a finite element model which approximates the dispersion and attenuation of the light signal as it passes to, and then through, the target tissue. The angles of the diverters are then set in order to produce desired optical stimulation patterns. In another example, the diverter 98 may be programmable and the paths of the beams can be adjusted after implantation by the medical practitioner. There may also be an upper 97 physical retainer and a lower physical retainer 99 that may be used to physically adjust the orientation of the optical SEST element 90 itself in order to angle the beams, although the retainers 97, 99 would most likely be adjusted prior to implantation since programmably adjusting these after implementation would require moving parts, which is undesirable in implanted devices.

FIG. 6B shows an exemplary variation of a programmable aperture 96, which is a "motionless aperture" because it does not require moving parts. This is implemented by a series of concentric disc elements 102a-e, each of which may be adjusted in order to prevent light from passing. Electrochromic qualities are provided at low voltage power, which may be supplied by power lines 106a and 106b (which may be operated to cause voltage reversal needed to switch from opaque to transparent states) that contact the individual disks at pairs of point contacts 104a-104e. The disks are each divided by a non-conductive, transparent barrier 105, so that the current travels between the pairs of point contacts 104a-104e to extend around the full circumference of the disk. The disk may be comprised of switchable glass technology such as two outer glass layers that flank a suspended particle device or electrochromic device having a multi-layer configuration (e.g., with an ion storage layer and an ion conductor layer sandwiched between two conducting oxide layers) or other alternative designs. Additionally, rather than a series of disks, switchable glass technology may be implemented in the form of a programmable grid of apertures, the elements of which may be made transparent or opaque (not shown). If a prism-shaped glass grid is placed in the pixels 84 of the interface plate 79, then the light may be dynamically routed to different areas of the prism-shaped glass grid within each pixel 84, in order to change the angle of the emitted light without requiring mechanical adjustment or movable components. Other methods of optical routing using low voltages and non-mechanical adjustment of the emitted light, are also possible.

FIG. 6C shows how optical stimulation may be implemented using a variation of a SEST-grid 26 which utilizes optical stimulators 90 which are angled to provide angled light from the SEST-elements 82b and subsequent summation in an intended target area of the cortex 110. In the figure, adjacent target areas 112 are stimulated at five different time intervals (Time 1-Time 5). At Time 1, three stimulators are used to stimulate a first target area 112a, and as time continues to the interval defined by Time 4, different elements 82b of the SEST-grid 26 are used to stimulate adjacent target areas 112b-112c. At interval Time 4, the optical element 90 uses either an aperture 96 or its lens 94 to produce a wider optical stimulation field so that the target area 112d is larger than that of 112a-112c. At interval Time 5, an optical element 90 is used that may have a programmable optical routing mechanism that allows the optical signal to be emitted from the SEST-grid element 82b over an angle defined by angle 108. In this implementation, SEST-grid 26 enables stimulation of target tissue, such as brain tissue, to take place using multiple light-emitters, which are placed to illuminate multiple points of target tissue, and to provide for controlled summation of the signals. Stimulation of target tissue can also occur by moving the target position of a single light source across a desired area, and the characteristics of the optical stimulation can remain constant or can be varied along this path.

There may be a number of advantages of configuring a skull-mounted ferrule system to provide optical stimulation through its SEST-grid 26 rather than via conventional (i.e., electrical) SEST-conduits 61. Firstly, the location and angle of the optical signal which is used can be adjusted during the course of therapy either by using programmable elements 90 or by changing which elements 90 provide the stimulation. In this manner, multiple optical signals can be used to stimulate the cortical surface with different spatial and spatial temporal patterns. This type of adjustment is not possible with conventional optical fibers, which are typically secured in a fixed position to stimulate a particular region of a neural target. This feature may also offer greatly improved stimulation performance compared to using a small number of optical fibers, each of which would normally be surgically implanted within the brain itself.

Placement of the SEST-grid directly under the implantable device may permit more accurate sensing of optical signals since a shadow may be cast by the implantable device (e.g., neurostimulator) onto the cortex. Normally, ambient light from outside the patient's head can decrease the optical sensing abilities of a skull mounted implantable device. Patterns of blood flow and oxygenation which are derived using optical techniques such as NIRS may also be further improved by providing an opaque flap, which may be part of the ferrule and located extracranially. The flap can be made of silicon or metal and assist in optical sensing from the cortical surface. Employment of an opaque flap may provide an advantage because it may increase the optical barrier, which in turn may increase the signal-to-noise level of the reflected optical signal that is sensed to obtain a measure of perfusion. Additionally, an optical probe which is located relatively distal from the SEST-grid 26 can also be used to measure global changes in light levels and this information can be used to subtract noise from the signals obtained from the SEST-grid 26 (in order to compensate for baseline drift and transient changes related to light sources or tissue states) which summate with the localized changes which are detected by the SEST-grid 26.

Placement of Sensing or Stimulation Probes

The ferrule system 1, its SEST-conduits 61, the SEST-grid 26, and other SEST-probes 438 that may be used to provide SEST functions may be placed within a portion of the cranium or a body tissue proximate the cranium in a number of different ways. Placement may occur using the results of both structural and functional imaging techniques such as, EEG, MEG, NIRS, fMRI, MRI, DTI, and regional perfusion imaging (RPI), which is an MRI procedure that matches cerebral arteries to flow territories and is designed to non-invasively provide standard perfusion and cerebral blood flow data, and determine the contribution of each artery as well as the role of collateral vessels. Functional neuroimaging techniques such as EEG or evoked potential mapping can be used to derive placement of SEST-grid and probes, and can also be used to evaluate and adjust post-implantation stimulation.

The location of implantation may depend on the type of data being sensed, or type of stimulation desired. The SEST-grid 26 and other SEST-probes of the device may be implanted above, within, or under an anatomical structure such as the skull, meninges, or cortical tissue of the brain. When implanted below the dura, either a biocompatible polymer film or a small intestinal submucosa (SIS) material (e.g., Durasis™) may be stitched into the re-sectioned dura, and used for dural layer replacement or modification so that implantation occurs without dura-related complications. When implanted above the dura, a section of dura may be removed to allow sufficient transmission of SEST-signals to their intended targets.

Calibration, Adjustment, and Evaluation of Therapy with Sensing and Stimulation Grids A number of brain disorders may benefit from the functional features of the SEST-grid. In recovery from stroke, particular spatial temporal patterns may be used to stimulate or facilitate intended movements or patterns of activity on the somatosensory cortex. For example, individual neural tracts may be stimulated at different times in a precise spatiotemporal pattern in order to produce a coordinated movement. Similarly, different neural elements may be stimulated in a spatiotemporal pattern to achieve or mimic desired patterns of neural activation or inhibition related to these movements. These spatiotemporal patterns may be adjusted by altering the timing or intensity of stimulation at each SEST-element in order to optimize a desired response, such as a sensation, movement, or decrease in symptoms in the subject. This strategy may also be used to produce or enhance fine motor activity. The SEST-grid allows precise control of stimulation patterns and can be used to investigate the functional results of these patterns.

In this manner, structures of the cerebral cortex can be mapped, especially with respect to the somatosensory cortex. Stimulation of different combinations of SEST-elements should correspond to different points on the cortical surface that are related to different points on the body surface. The SEST-grid can both sense and stimulate these regions to provide spatial-temporal patterns of activity in cortical tissue related to sensor/sensory motor processes. By applying stimulation patterns that mimic or adapt to activity, e.g., endogenous patterns and evolving patterns, which can occur in a plastic manner during stroke recovery, stroke therapy may be improved.

The SEST-grid 26 is advantageous for the mapping of cortical or other brain tissue by systematic perturbation of different tissue regions under the SEST-grid. Stimulation of a target location can produce results that may be observed by the physician and/or the patient and stimulation induced changes in subjective perception or movement can be used to design the therapy. By iteratively repeating this procedure, a map of the functions of different brain areas may be generated. Stimulation of brain areas that results in an adverse effect are to be avoided.

A particular application for which a SEST-grid may be useful is in the detection, and responsive stimulation, of cortical depression. Cortical depression is a cortically based (or at least cortically observable) phenomenon wherein a wave of activity travels across the cortex in a particular direction and in a particular rate. In order to accurately detect and quantify cortical depression either a plurality of conventional SEST-conduits must be implanted or an SEST-grid can be used. A SEST-grid is particularly well oriented towards both the detection of the cortical depression as well stimulation treatment. Since cortical depression has been reported to often have an approximately constant speed and direction, these characteristics can be used to identify or predict the emergence of this event and to adjust the, timing of the stimulation, location of stimulation, the spatial or spatial temporal stimulation pattern which is used (when multiple elements are used in the stimulation) to disrupt the spread of this activity. The SEST-grid 26 is useful in sensing information which will allow the spread of activity to be assessed. Whether electric, sonic, optical, or other type of SEST-functions are implemented by the SEST-grid, spatial and spatial temporal sensing and stimulation are relevant for treatment of these, and other disorders of the brain.

Figure 7:
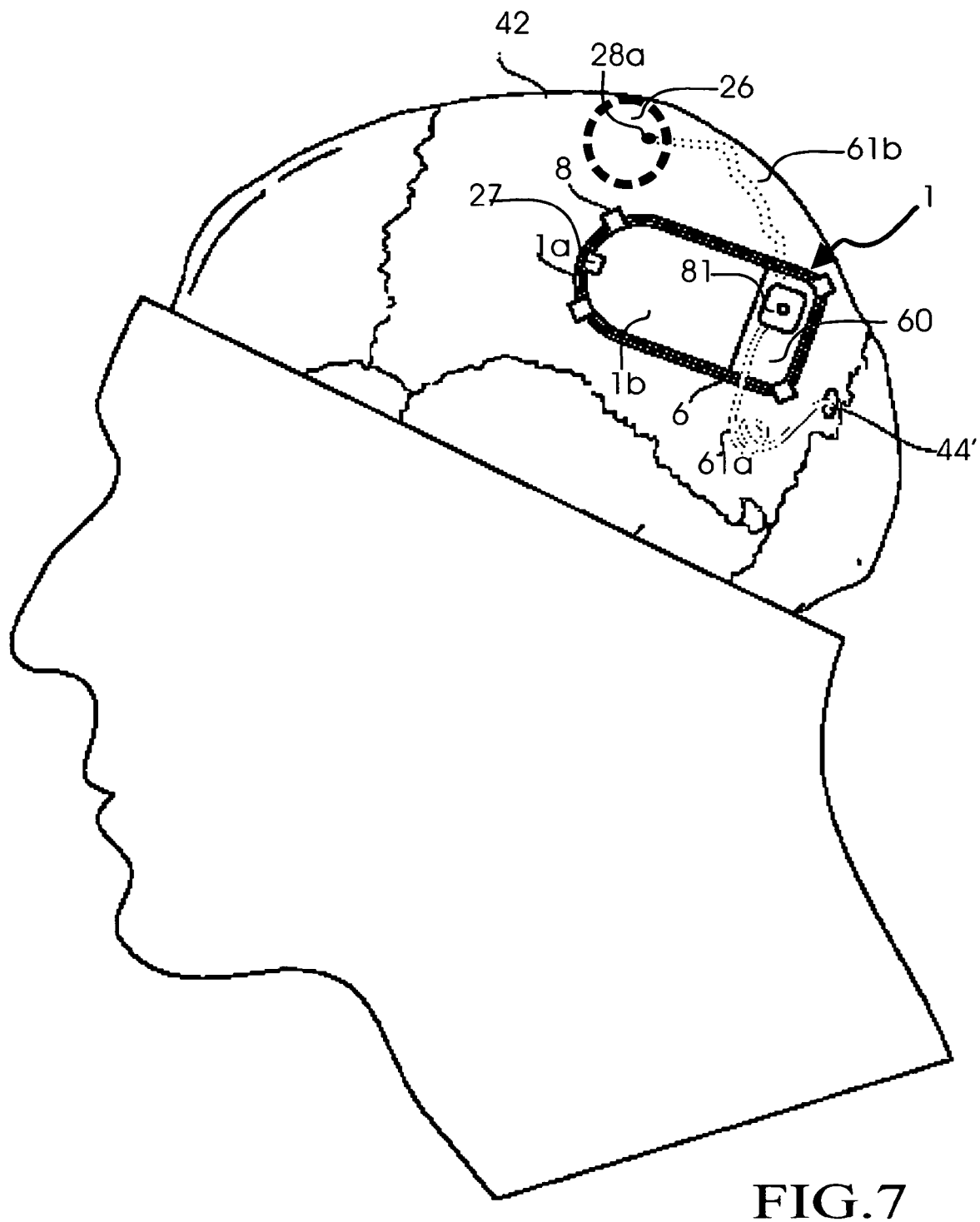
FIG. 7 is a perspective view of a system for sensing and stimulation having a skull-mounted SEST-grid at a different location than that at which the system is secured.

FIG. 7 shows a variation of a ferrule system 1 in which a SEST-grid 26 is implanted in the cranium 42 of a patient at a different location than the implantable device (neurostimulator) 1b. The SEST-grid 26 may be used in an extra-cranial (e.g., as may occur in the case of a sonic transducer), intra-cranial, or sub-cranial configuration, and may also utilize a ferrule device or may be secured in position in an alternative manner. The SEST-grid 26 communicates with the device via a device-grid control connector 28a which accepts the distal end of a SEST-conduit 61b, which exits the device from a conduit slit (not shown) located on the dorsal side of the conduit storage area 60 and which is covered by slit cover 81. Also shown is conduit 61a, which travels through burr hole 44' and is implanted within the brain of the patient. The burr hole 44' is sealed after implantation to prevent further movement of the conduit 61a and in another variation, a burr hole cover or burr hole plug is affixed to the cranium 42 and resides at least partially within the burr hole 44' itself to provide this functionality. In this aspect of the invention the ferrule system 1 may be provided with a distally located SEST-grid 26 and the implantable device 1b communicates with the SEST-grid 26 via a ferrule-grid connection provided in the ferrule or directly using a device-grid connection, either of which may be realized using conduit 61b. The variation shown in the figure may be useful, for example, when the SEST-grid 26 provides thermal stimulation, so that the device 1b or its power source, are not exposed to temperature fluctuations. Further, this variation is also useful when the SEST-grid 26, contained on the ventral surface of the ferrule system 1, works in conjunction with at least one other SEST-grid 26 located elsewhere.

Figure 8:
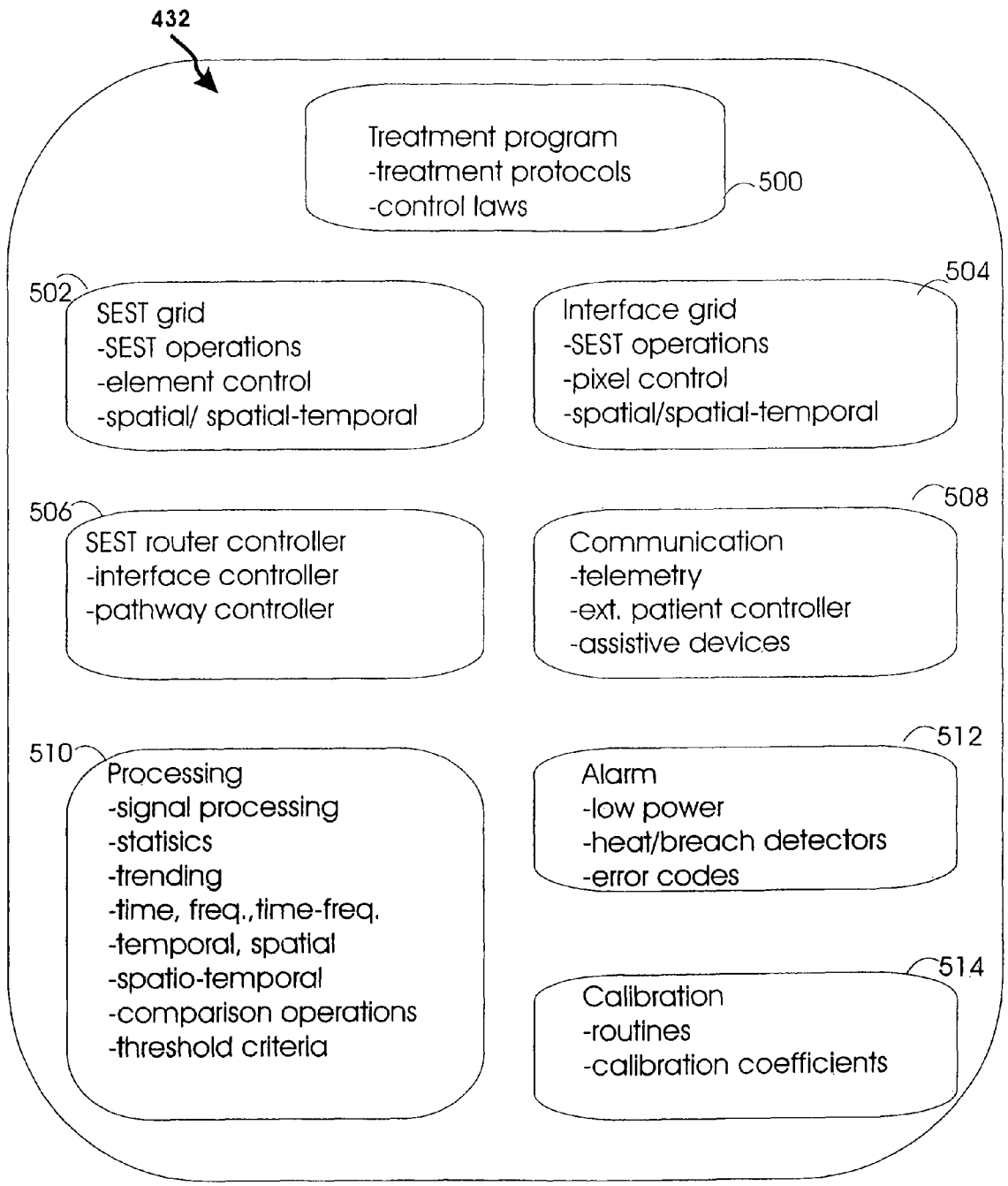
FIG. 8 is a block diagram of functional modules of the control subsystem.

FIG. 8 shows a schematic illustration of a control subsystem 432 used in one variation of the ferrule system 1. The control subsystem 432 implements the treatment program 500 which includes all algorithms, settings, and protocols needed to accomplish operation of the ferrule system I in the provision of treatment. The treatment protocol includes the sensing, evaluation and stimulation protocols, and the parameter settings which are used by those respective subsystems during treatment, and thereby allows the control subsystem to control and coordinate all functions carried out by various subsystems of the ferrule system 1. The treatment protocol also includes control-law algorithms derived from characteristics of sensed data that provide control signals, as implemented by other known methods. The SEST-grid module 502 controls all SEST-grid functions including controlling the sensing and stimulation subsystems to permit sensing and stimulating using the SEST-grid 26. The SEST-grid module 502 also contains algorithms for specific spatial or spatial-temporal patterns of stimulating or sensing using the SEST-grid, as well as the SEST-conduits 61 and SEST-probes 438 which may be used, separately or in conjunction with the SEST-grid 26. The SEST-grid module 502 may also control the SEST-grid manager 416 in order to alter the properties of any of the SEST-grid elements. For example, if the elements are optical, then the SEST-grid module 502 may cause the SEST-grid manager 416 to alter the type of light, intensity of light, lens characteristics (e.g., distance between 2 or more lenses) aperture/shutter settings, and may adjust the angle of the emitted light using various control mechanisms that are present on the SEST-grid 26 variation being used by the ferrule system 1. The interface grid module 504 may also control the SEST-grid manager 416 in order to control the SEST-grid interface 79' and its pixels 84. The SEST-router module 506 controls routing of SEST signals. In the case of drug therapy, these can include "fluid signals," in the case of optical therapy these can include "light signals," and in the case of electrical therapy these can include "electrical signals." However, the router 506 can also route SEST-signals, which include any communication or command signals, and power which are routed to provide treatment. The SEST router module 506 may control the routing of signals between components of the ferrule system 1, including, but not limited to, the ferrule 1a, the device 1b, the SEST-grid 26, probes 438, and SEST conduits 61. The SEST-router 506 may also control the routing of signals created by external devices (e.g., an implanted laser) to different areas of the ferrule system used to provide therapy. In addition to controlling the routing path, the SEST-router module 506 may also control the rate (including a rate of zero where an SEST signal is not routed at certain times) and pattern of routing of the signals. The SEST-router module 506 may control the interface connectors (e.g., device-ferrule interface) to modulate the patterns of SEST-functions. The communication module 508 controls communications of the communication subsystem such as can be provided telemetry or physical links with external devices (e.g., the external patient programmer) and also provides for communication with other implanted devices which may be assistive devices. For example, the communication module 508 may send a signal to an assistive device such as an implanted drug pump so that it delivers a particular type of drug through SEST conduit 61, to the ferrule system 1 and this drug then is routed under the control of the SEST router controller module 506 to a desired location on the SEST-grid 26. The control subsystem 432 also contains a processing module 510 for performing signal processing, statistics, and trending of sensed data and historical stimulation activity. For example, the processing module may keep a record of past detected events and if it processes this "event history" and detects a recent increase in event frequency which is above a specified rate, or which meets a statistical criterion indicating an increase in events over time has occurred, then a change in stimulation protocol may be implemented according to the algorithms of the treatment program. Further, a specific spatial pattern of stimulation may be defined to occur in response to the evaluation of sensed data which indicates a specified spatial pattern of neural activation (e.g., the area of tremor activity spreads beyond a specified cross sectional area, as detected by an increasing number of sensing elements on the grid) has occurred. The processing module 510 can detect these patterns of sensed data and may be configured to operate as part of the control subsystem 432. The processing module can also provide filtering of data, and other signal processing operations including time and time-frequency analysis of the data, including detection of energy provided by a detection module (e.g., detection module 424 in FIG. 9). The processing module 510 can also be used to compare sensed data to a detection criterion in order to detect a medical event defined as requiring stimulation. The control subsystem 432 may rely on the processing module to accomplish at least a portion of the evaluation of data. Another module is the alarm module 512, which may cause the communication module 508 to send an alarm to the external patient programmer or may send an alarm to an acoustic stimulator of the device 1b if it detects that something has occurred for which an alarm should be triggered. For example, if the power supply of the ferrule system falls below a specified level, or if the temperature of the implantable device 1b exceeds a selected level (e.g., while providing cooling stimulation), or if error codes are generated by error detecting algorithms in the various subsystems of the device 1b, or if a breach detector which may be located in areas such as the conduit storage area 60, indicates, for example, due to increased moisture, that the device has experienced a breach. Additional sensors or circuitry may be provided to detect electrical shorts or fluid leaks between plug contacts of interface connectors, and to issue an alarm if such malfunction occurs.

Figure 9:
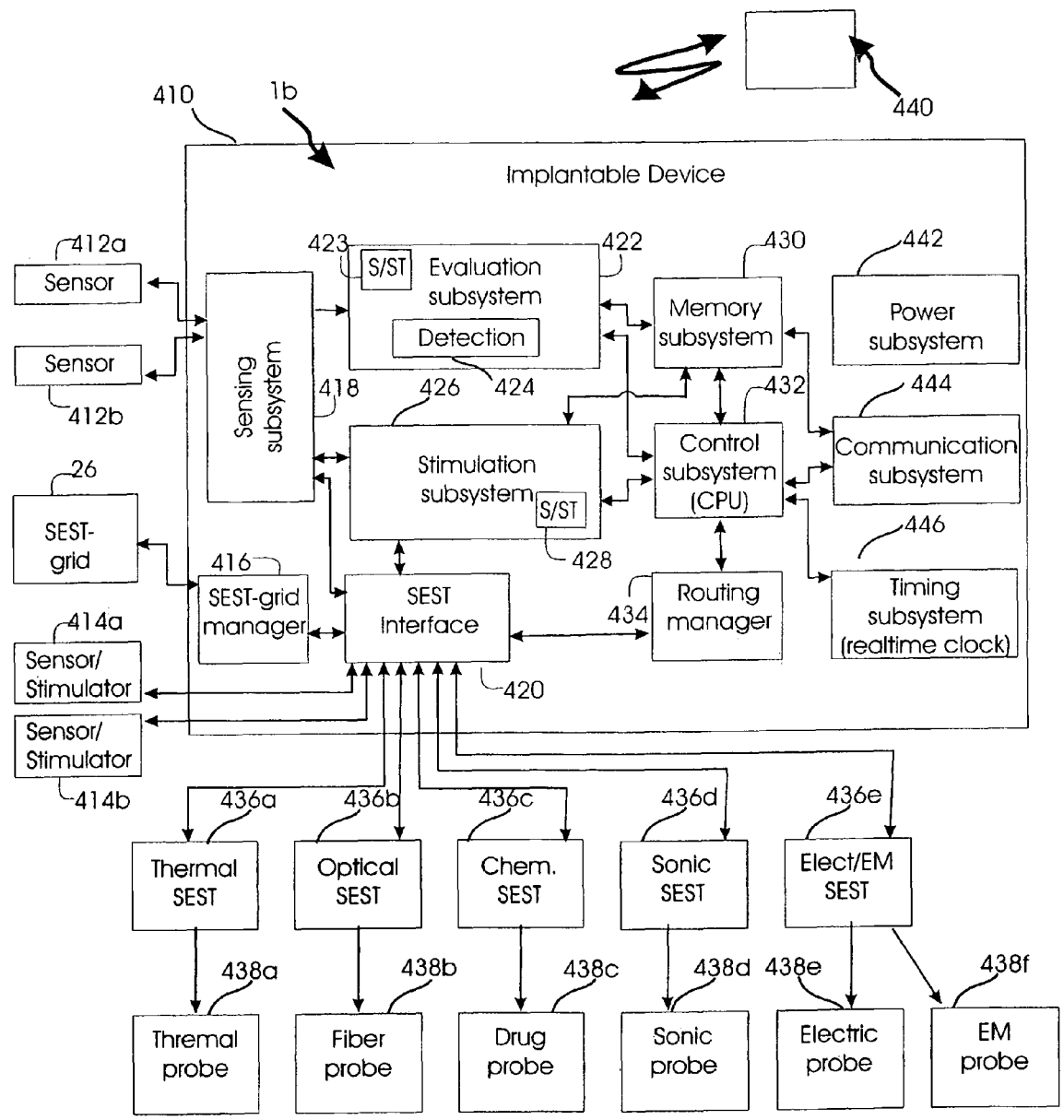
FIG. 9 is a schematic illustration of an exemplary system for sensing and stimulation.

FIG. 9 is an overall block diagram of the implantable device 1b used for providing functions such as sensing, evaluation, detection, control, and stimulation. In housing 410 of the device 1b several subsystems and components work together to provide therapy. The device 1b is capable of being coupled to a plurality of sensor probes 412a, 412b, as well as sensor/stimulator probes 414a, 414b. In one variation, the sensors/stimulators may be conduits including electrical leads that may be used for both sensing and stimulation (e.g., electrodes) and may also provide for the delivery of more than one treatment modality when the conduit communicates with more than one type of probe 438. In the illustrated variation, the physical and electrical coupling for sensing may be accomplished through a conduit connector, which preferably is located in the conduit storage area 60, and which relays the sensing and stimulation signals to the sensing subsystem 418. Although two sensors (412a and 412b) are shown in FIG. 9, any number of sensors is possible. It is also possible to utilize one or more SEST conduits, each having at least two electrode contacts, or in another variation, two conduits, each having a single electrode contact (although bipolar sensing and stimulation operations including sensing between two closely spaced electrodes on a lead may be preferred to minimize common mode signals including noise). Additionally, sensing and stimulation may be accomplished by SEST elements 82 of the SEST-grid 26 which communicates with the sensing subsystem 418 or the stimulation subsystem 426 using the SEST-interface 420, which is under control of the routing manager 434. The SEST-grid manager 416 controls the circuitry and elements 82 of the SEST-grid 26, and also the pixels 84 of the interface plate 79 if a grid with pixels is utilized. The sensor probes 412 may communicate directly with the sensing subsystem 418 while the sensor/stimulator probes 414 communicate signals through the SEST-interface 420 so that both sensing and stimulation signals are routed accordingly. The probes 412, 414, and 438 may be in contact with the patient's brain or are otherwise advantageously located to provide various SEST functions.

Sensed data may be comprised of ongoing activity or activity related to stimulation (e.g., a short post-stimulation blanking period may be used to avoid saturation of the amplifier when both sensing and stimulation are in the electrical modality). Sensed data may include, but are not limited to, EEG data, neuronal recordings (e.g., single neuron recordings, nerve potential recordings, local field potential recordings), ultrasound and doppler shift ultrasound data, oximetry data, optical sensing data, blood pressure recordings, impedance measurements, measurements of blood gases or chemical composition, measurements of temperature and acceleration, measurements of emitted or absorbed radiation (e.g., infrared spectroscopy measurements and spectrophotometric measurements), and combinations thereof.

The SEST-interface 420 may also provide components and circuitry to accomplish features generally present in sensing subsystems including but not limited to amplification, isolation, analog to digital conversion, multiplexing functions on the signals in the SEST channels of probes, and charge-balancing functions, that are required for a proper interface with neurological tissue and which are not provided by any other subsystem of the device 1b. After sensed data are digitized, these are evaluated by the evaluation subsystem 422 in order to provide quantified measures of the data which may be compared to thresholds or used by control laws, and which may generally be used to adjust therapy, or provide closed-loop or other type of responsive treatment. Closed-loop implementations can use sensed data of one modality to provide stimulation in another modality. Evaluation of sensed EEG data may be used to select optical stimulation signals and thereby provide "multi-modal physiological" control of stimulation parameters. The evaluation subsystem contains a detection module 424 with algorithms for identifying medically relevant events, which can lead to stimulation treatment according to the therapy program of the control subsystem. In one variation, electrographic signals are received by SEST conduits, such as electrodes, and a detection subsystem 424 includes an EEG waveform analyzer that can implement both time and frequency analysis for detecting characteristics of the waveforms that have been defined as requiring adjustment or provision of stimulation (e.g., as described in U.S. Pat. No. 6,016,449 to Fischell et al. and U.S. Pat. No. 6,810,285 to Pless et al., which are hereby incorporated by reference in their entirety). Similar detection algorithms may be applied to the analysis of other types of waveforms received from other types of sensors. Evaluation of the sensed data, including detection and quantification of events, may occur using time, frequency, time/frequency analysis and other signal processing strategies that are programmed into algorithms of the evaluation subsystem 422 and processing module 510 of the control subsystem 432. Evaluation of sensed data is generally accomplished in conjunction with a control subsystem 432 which contains a central processing unit (CPU). The evaluation of data can occur for different locations in space (e.g., for different elements of the SEST-grid), and across time. For instance, the detection module may detect a type of abnormal activity at a sensor near the left side of the SEST-grid, and over time it may both increase in amplitude and also be increasingly sensed by sensors near the right side of the grid (indicating either movement of the source or change in orientation of the dipole). This pattern of activation may result in a unique stimulation treatment that is responsively provided when the activity is detected according to a different spatial or spatial temporal pattern. The analysis of spatial/-temporal patterns can be accomplished by the S/S-T module 423 and/or the SEST-grid module 502 of the control subsystem 432. The evaluation system 422 and its detection module 424 may contain a plurality of evaluation and detection capabilities, including but not limited to analyzing measures derived from physiological conditions (such as electrophysiological parameters, temperature, blood pressure, neurochemical concentration, etc.) either jointly (e.g., electrical and optical data are combined to assess events) or in an independent fashion (e.g., electrical and optical data are each evaluated separately to assess events).

The stimulation subsystem 426 is capable of applying stimulation to neurological tissue using a number of different types of SEST-modules 436a-436e, each of which communicates with SEST-probes 438a-e, which may be implanted into different target locations or which may exist on the SEST-grid 26 as SEST-elements. The SEST-modules 436 and their probes 438 can provide both sensing and stimulation when the routing manager 434 controls the SEST-interface 420 in order to establish communication with either the sensing 418 or stimulation 426 subsystem. Similar to known devices, stimulation can be programmed to occur as a substantially continuous stream of pulses, on a scheduled basis, responsively using a predefined stimulation protocol or a protocol which is adapted based upon a characteristic (e.g., the size) of the measured data and of the detected events (e.g., using proportional control laws with minimum thresholds which do not output a control signal until a characteristic of an input signal reaches a specified threshold related to the detection of an unwanted type of activity), and in other manners dictated by the treatment protocol. In another variation, scheduled therapy (such as stimulation provided via biphasic pulses or low-frequency sine waves) may be performed by the device 1b in addition to, and independent of, responsive therapy. The therapeutic stimulation may be provided in response to abnormal neurological events or conditions detected by a waveform analyzer of the detection subsystem 424. The SEST functions and signals may be determined by the treatment program 500 of the control subsystem 432. A plurality of stimulation and sensing modalities may be used including, for example, electrical, chemical, optical, thermal, sonic (including ultrasonic), audio, visual, or tactile signals as well in order to provide somatosensory stimulation to locations other than the brain. Stimulation signals may be used as well in order to provide somatosensory stimulation directly, or may be provided to locations other than the brain, for example, in order for the patient to experience the sensory stimulation. Chemical stimulation may include a drug or other therapeutic agent (used either alone or in conjunction with other types of stimulation including stimulation which can activate the drug). Any of these therapies may be provided in a non-responsive therapy modality, such as scheduled therapy, either alone or in combination with a responsive therapy regimen.

The implantable device 1b contains a memory subsystem 430. The control subsystem 432 may control the operation of (and store and retrieve data from) the memory subsystem 430. In one variation, the memory subsystem is realized in the form of, or includes, a queryable database. The memory subsystem 430 may be coupled to various components, including the evaluation subsystem 422 for receiving and storing data representative of sensed signals. The memory subsystem 430 may not only contain historical records of sensed events, but may also contain protocol settings, customizable stimulation routines, normative data, threshold settings, and other settings, data, and operations which are stored and retrieved during the provision of therapy. Data stored in a memory subsystem 430 may be retrieved by the patient's physician or patient through the communication subsystem 444. A software operating program run by the external patient programmer 440 allows the physician to request the sending of historical events and data including sensed information before, during, and after each neurological event, as well as specific information relating to the detection of each neurological event (such as, in one variation, the time-evolving energy spectrum of the patient's EEG). The programmer 440 also allows the selection and adjustment of any programmable parameters used by the treatment program 500. The control subsystem 432 contains a CPU, which can take the form of a microcontroller and microprocessor. The control subsystem 432 is functionally connected, either directly or indirectly, to the evaluation subsystem 422, the stimulation subsystem 426, the sensing subsystem 418 (in the figure may occur via the SEST interface 420), the memory subsystem 430 and all the other subsystems and components within the device 1b, for achieving control and communication operations.

A communication subsystem 444 enables communication operations that are necessary for therapy. This may include communication between the device 1b, and implanted SEST components that are external and not physically connected, to the device 1b as well as the outside world, particularly the external programmer 440. The communication subsystem 444 may include a telemetry coil (which may be situated outside of the housing of the implantable device 1b) enabling transmission and reception of signals, to or from an external apparatus, via inductive coupling. Alternative variations of the communication subsystem 444 may use an antenna for an RF link or an audio transducer for an audio link. Preferably, the communication subsystem 444 includes a GMR (giant magnetoresistive effect) sensor to enable receiving simple signals (namely the placement and removal of a magnet) from a patient programming device. Communication ranges of up to a few meters and potentially more are possible.

In another variation, a long-range telemetry RF link operates in the MICS (Medical Implant Communications Service) band at approximately 402-405 MHz. This band is well suited for communication within and around the human body and is available for use in the United States without a license.

A power subsystem 442 may include a power supply that supplies the voltages and currents necessary for each of the other subsystems to function. The power subsystem may also contain circuitry for discharging or recharging the battery (e.g., via induction) and circuitry for indicating how much power is left, and this data can be sent to the memory subsystem 430. The routing manager 434 may control not only the SEST interface in order to route the SEST-signals to the appropriate subsystem, but may also control the device-SEST interfaces (e.g., control interface connector 28a, and signal connector 30a) and the pathway controller that may be embedded within the conduit storage area 60. The timing subsystem 446 supplies substantially all of the other subsystems with any clock and timing signals necessary for their operation, including a real-time clock signal to coordinate programmed and scheduled actions and the timer functionality used by the detection subsystem 424 that is described in detail below.

In another variation, the stimulation subsystem 426 is coupled to a number of SEST modules that control SEST probes. FIG. 9 shows a thermal SEST module 436a, an optical SEST module 436b, a chemical SEST module (which may include a reservoir) 436c, a sonic SEST module 436d, and an electrical/electromagnetic SEST module 436e. Additional SEST modules 436 are also possible. The thermal probe 438a contains an SEST element which can be a thermally conductive surface. In one variation, the thermally conductive element may use material having high thermal conductivity and low thermal mass, and may be coated with a thermally-conductive material that is biocompatible. The optical probe 438b contains an SEST element, which may be an optical fiber located within an SEST conduit 61, and may have optical adjustment components such as a programmable aperture or biocompatible lens at its distal tip through which light is presented. The chemical probe 438c may be a stimulation conduit which is a catheter that may or may not have valve devices for outputting drugs at specified stimulation output sites, as well as a chemical sensor. The provision of spatial/spatial-temporal (S/S-T)patterns of stimulation can be accomplished by the S/S-T module 428 of the stimulation system, as may be required by different stimulation protocols.

Any of the therapies delivered by the stimulation subsystem 426 are delivered to a stimulation output site. It should be recognized that the therapy output may be a stimulation electrode, a drug dispenser outlet, or a thermal stimulation site (e.g., Peltier junction or thermocouple) as appropriate for the selected modality. The stimulators may be located within the device 1b, or may be implanted elsewhere and controlled by the device, and may also deliver stimulation therapy themselves or the stimulation signals may be routed through the device using the pathway controller 70 which is controlled by the routing manager 434. For example, the device 1b may control a drug pump to supply drug via a SEST conduit 61a to the stimulation device, which then routes the drug to another SEST conduit 61b for delivery of the drug at a particular catheter stimulation output site 438c. The output sites 438c may exist as stimulation elements of the SEST-grid 26, when these are formed within the surface of the SEST-grid.

In one variation, the relay pathway system 68 and pathway controller 70 are embodied in a separate routing device that is controlled by the routing manager 434. An external device, such as a drug pump may provide its drug through the input conduit 61d of the routing device, which then controls the routing of the fluid SEST-signal including the rate, pattern, and path of the SEST-signal as it is transmitted to one or more output SEST-conduits 61e. If the pathway controller 70 communicates with the ferrule 1a, and this communication is relayed to the device 1b using a ferrule-device interface, then the device 1b can be replaced without modifying the drug pump, the input conduits, the output, conduits, the pathway controller 70, or any of the connections between these components.

A probe may include at least one stimulation element or at least one sensor element, or at least one of both. The probe may also contain processing circuitry for accomplishing the sensing and stimulation and for switching between the sensing and stimulation activities and for transducing the signals. In the various types of sensed data described herein (e.g., electrical impedance plethysmography, etc.) the data is often measured relatively, such as according to baseline measurements, rather than as an absolute value, and can also be adjusted (e.g., calibrated) according to measured variance so that the signals are meaningful. Further, in the evaluation subsystem 422 of the device, compensation for heart-rhythm-based variations (e.g., heart rate may be measured by taking average or peak values over several measurements), activity level, body position, and time of day may also be deemed advantageous in the evaluation of sensed data. The location of the probe (e.g., 438a) is usually treated as the approximate output location of the sensing and stimulation, respectively. In the case of chemical therapy, the stimulation part of the probe can be the distal end of an SEST conduit (e.g., a catheter tip) which may contain a valve structure for regulating flow and components for deterring clogging and accumulation around the output. The sensing probe can be a chemical sensor which communicates with the sensing subsystem of the device 1b, via an electrical lead that spans the length of the catheter and attaches to the sensor interface of the sensing subsystem.

In an alternative variation, electrodes are used in combination with other sensors, such as temperature and blood flow sensors, as will be further described below. In another variation, one or more of the sensor probes 412 may be an electrochemical sensor, a temperature sensor, or any of a number of sensor types capable of measuring cerebral blood flow, oxygenation, or any other local physiological condition of interest as disclosed in U.S. patent application Ser. No. 11/014,628 to Pless et al. which is hereby incorporated by reference in its entirety. The sensor may also be a biochip or pH sensor. Some sensors that may be used by the device have been listed in U.S. Publication No. 2005/0277912 to John, which is hereby incorporated by reference in its entirety. The sensor may be any sensor that permits the measurement of neurochemicals in vivo, including, but not limited to sensors that may be used in microdialysis, constant potential amperometry, various types of voltammetry, high-speed chronoamperometry, or any number of electroanalytical techniques known in the art. The sensor may detect at least one of: intra-cellular or extra-cellular concentrations of neurochemicals, chemicals in blood or CSF, as well as other regions of the fluids in the brain or body of the patient. If the evaluation of sensed data by the evaluation subsystem 422 indicates that a measure of neurochemical measured by the sensor is different from a specified amount (e.g., the measure is above/below a threshold criterion), then the control module can control the stimulation subsystem 426 to provide therapy until the neurochemical measurement matches the specified amount.

While the subsystems and modules of the ferrule system are shown in specific locations and have been described individually, they may also be provided in an integrated fashion. For example, the control, sensing, evaluation and stimulation subsystems may all be realized on a single customized chip that has been designed to accomplish the functions described herein. The subsystems may be implemented primarily in hardware, in specialized software, or in both. Further, although the memory subsystem 430 is illustrated in FIG. 9 as a separate functional subsystem, the other subsystems can utilize this subsystem 430 when these require various amounts of memory to perform their operations.

A plurality of ferrule systems may also be used to perform one or more functions on neural tissue. Each ferrule system may be operated independently, or may communicate to provide synchronized stimulation, for example, as may occur when a ferrule system is implanted in the cranium of each hemisphere and delivers therapy to each, respectively. The implantable device 1b may comprise a plurality of spatially separate units each performing a subset of the capabilities described above, some or all of which might be external devices not suitable for implantation.

In one variation, the ferrule system 1 may communicate with an external programmer 440 controlled by the patient or a caregiver. The patient may operate the programmer 440 to cause the ferrule system 1 to switch modes ('on' to 'off' and vice versa, for example) or perform an action (e.g., store a record of EEG data). The communication system 444 may rely solely upon unidirectional communication (as with the magnet and GMR sensor), only allowing commands to be received from the programmer 440, but may also rely upon bi-directional communication. The programmer may be a specialized, programmable, and hand-held computing device or may simply be a permanent magnet if the communication subsystem 444 is adapted to identify magnetic fields and interruptions therein as communication signals.

Optical Sensing and Stimulation

Optical energy has been used for various medical and surgical purposes for over a half-century. "Phototherapy" includes interventions such as using light for ablating tissue, treatment of blood disorders, activation of drugs, modulation of cellular and metabolic processes, and various other medical interventions. Laser light, or "coherent light", has been shown to evoke action potentials in neurons. Neural stimulation with light may also be referred to as "photostimulation" and can cause both excitation and inhibition (e.g., block) of activity. Different wavelengths have been demonstrated to modulate both peripheral and central nerve activity using a number of experimental preparations. For example, early on, Fork reported direct stimulation of nerve fibers using low-energy laser light (Fork, R., "Laser stimulation of nerve cells in Aplysia", Science, March(5): p. 907-8, 1971.) Laser stimulation of the abdominal ganglion of Aplysia Californica evoked activity during both light onset and offset. Since then, other studies have continued to explore photostimulation using a number of paradigms to explore how light stimulation modulates neural activity, nerve activity, and processing of peripheral stimuli. These have found parallels to what occurs when using electrical stimulation (e.g., Safavi-Farokhi Z, Bakhtiary A H. The effect of infrared laser on sensory radial nerve electrophysiological parameters. *Electromyogr Clin Neurophysiol.* 2005 September-October;45(6):353-6). Allegre et al. used ultraviolet radiation to evoke responses in rat nervous fiber bundles (Allegre, G., S. Avrillier, and D. Albe-Fessard. Stimulation in the rat of a nerve fiber bundle by a short UV pulse from an excimer laser. *Neuroscience Letters*, 180(2): p. 261-4, 1994). The energy required for stimulation was close to the amount which could cause tissue damage. Pulsed infrared light has also been used to excite neural tissue (generate action potentials), and has been shown to have good safety characteristics. Damage occurred at 250% of the intensity needed to surpass stimulation threshold at wavelengths corresponding to valleys in the IR spectrum of soft tissue absorption (i.e., 4.0 and 2.1 micrometers) indicating that a large range of intensity can be used without causing neural damage (Wells J., Kao C., Jansen E. D., Konrad P., Mahadevan-Jansen A. Application of infrared light for in vivo neural stimulation. *J Biomed Opt.* 2005 November-December:10 (6):064003). Laser stimulation has also been shown to induce action potentials in the auditory nerve, suggesting future uses of this technology in cochlear implant devices (Izzo A. D., Richter C. P., Jansen E. D., Walsh J. T. Jr. Laser stimulation of the auditory nerve. *Lasers Surg Med.* 2006 Jul. 26:38(8):745-753). Laser and light stimulation of neural tissue have been reported using such terms as "optical biostimulation," "low-level light therapy" (LLLT), "radiant exposure therapy," and "illumination therapy." When light is used to stimulate chemicals (e.g., photostimulated dyes) this has been termed "photoactivation" and is also known as photodynamic therapy, or PDT.

When stimulated using a laser pulse transmitted through an optical fiber, neural responses may approximate those obtained using comparable electrical stimulation. Similar to electrical stimulation the strength of the optical stimulation can produce various changes, and light stimulation must occur at an intensity and duration that is above threshold levels while being below levels which cause tissue damage or ablation, mainly due to heat buildup in the tissue. For all types of optical stimulation used by the ferrule systems described herein, the sensors may be used to monitor the stimulated tissue and ensure that stimulation occurs at the intended level and does not induce heat, activity, or cellular processes that are related to cell damage and death due either to direct effects of stimulation or excitotoxicity. A module such as calibration module 514 of the control subsystem may be used to verify optical stimulation characteristics sensed by thermal, optical, or other sensors and can be used to create calibration coefficients that can adjust the stimulation accordingly. Specific calibration routines may be used, which do not necessarily provide therapy, in order to automatically calibrate and adjust the optical stimulation parameters used during treatment. Laser light has advantages over other forms of stimulation because: 1) it can stimulate a precise location at predetermined range of energy levels; 2) it can increase the stimulation levels over a limited range without increasing the field of stimulation; and 3) it does not suffer from sensor-tissue interactions.

Laser light is approximately monochromatic or "coherent" and can provide selective stimulation of various anatomical targets which absorb this light. Although laser light is usually preferable, coherent and non-coherent light in the visible range as well as other ranges of the spectrum may be used by the device. The ferrule system 1 may use a tunable laser, which permits wavelengths to be generated for selective absorption by tissue, increasing the likelihood of relatively selective stimulation. Light absorption depends upon certain characteristics of both the tissue and the light, but the reflectivity, absorption coefficient, and scattering coefficient may be optimized by adjusting the wavelength used for providing the energy in relation to the tissue being treated.

A "treatment model" may be used to choose the stimulation parameters of the optical stimulation and this model can be based upon the patient's neuroimaging data. This module can be used to adjust the stimulation protocol to the individual patient by adjusting angle, intensities, and other characteristics of the light therapy which is to be used. Additionally, phantom brains (e.g., fluid models approximating the physical characteristics of the skull, surrounding tissue, and brain tissue) and mathematical models such as finite element analysis can be developed to model, and thereby adjust, light therapy so that it stimulates the intended targets in the intended manner.

Different lasers can be used to provide different wavelengths used in treatment and some of the candidate laser types and exemplary characteristics are included in the following table:

| Type | Wavelength | Spectrum | Targets |
| --- | --- | --- | --- |
| Ruby | 694 nm | Red portion of the visible spectrum. | Blood hemoglobin. Not water or non-pigmented tissue. |
| Argon | 488 nm, 515 nm | Red portion of the visible spectrum. | Blood hemoglobin. Not water or non-pigmented tissue. |
| Carbon | 9.4 mm or | Invisible, far infrared | Water and other tissue relatively |

-continued

| Type | Wavelength | Spectrum | Targets |
|---|---|---|---|
| dioxide | 10.6 mm | portion of the electromagnetic spectrum. | independently of tissue color. |
| Neodymium doped yttrium-aluminum-garnet (Nd:YAG) | 0.94 mm or 1.6 mm | Near infrared portion of the electromagnetic spectrum. | Blood hemoglobin. |

Most laser systems are still relatively large and have power requirements beyond that useful for implantable or portable variations. Due to the size and energy requirements of laser sources, a transdermal fiberoptic connection using an externally located light source may be implemented, similar to the design relied upon by some insulin pumps and other percutaneous stimulation systems. The light source can be a benchtop laser system as may exist in a clinic, wherein the implanted device uses the light from this external laser, which is transmitted through the implanted devices using optical fibers, during treatment periods. This may occur during rehabilitation treatment obtained for stroke recovery or in the treatment of other disorders. While it is clear that optical energy can be used to stimulate tissue, a number of barriers remain in its clinical implementation within implantable devices. The main issues are energy requirements, versatility, size and cost, of the optical source, which is normally a laser. Progress has been made on solving these issues (e.g., low power laser diodes), and the miniaturization of light sources has progressed at a rapid enough pace that a portable, if not fully implantable, optimally based neurostimulation system is certainly realizable.

The light source may be implemented in a number of ways, ranging from fully implantable devices, to semi-implanted devices, to existing as fully external light sources. Fully implanted devices may use diodes or other light emitters, while semi-implanted devices may utilize externally worn lasers that relay the light using transdermal optical fibers. Some initial designs for handheld devices have been developed, such as those described in U.S. Publication No. 2005/0216072 to Mahadevan-Jansen et al., which is hereby incorporated by reference in its entirety. This publication describes combining laser stimulation with electrical stimulation to improve depth of penetration in the tissue. Alternatively, diode lasers can provide coherent optical energy and are more likely to be used in portable medical devices. As described in U.S. Pat. No. 6,033,431 to Segal, which is hereby incorporated by reference in its entirety, one such diode laser (In: GaAs diode laser), can be used and as indicated in the specification, and the amount of Indium with which the Gallium Arsenide in the diode is doped can be made appropriate to cause the wavelength of laser light generated by the diode to be in a range between 1.06 mm and 2.5 mm, which can be useful in medical applications. U.S. Pat. No. 6,872,221 to Lytle, and U.S. Publication No. 2004/0073278 to Pachys, both of which are hereby incorporated by reference in their entirety, also review a number of types of phototherapy used in the various medical treatments and describes a number of various light sources, some of which may be hand-held, and therapeutic parameters (e.g., wavelengths) used for stimulating different anatomical targets and modulating various biological processes. U.S. Pat. No. 6,925,328 to Foster et al., which is hereby incorporated by reference in its entirety, describes an optical device in which the light signal is used for communication between a device and its electrical stimulators, rather than for stimulation itself. However, as described herein, this system may be implemented and adapted to provide optical stimulation of target tissue. A free-electron laser (FEL) which may be tunable can be used to provide therapy and to assess the optimal wavelengths for optical stimulation or therapy. As described in U.S. Publication No. 2006/0155348 to deCharms, which is hereby incorporated by reference in its entirety, the FEL may utilize a train of 1-picosecond energy spikes, called "micropulses", which occur rapidly enough that these are considered continuous with respect to neural tissue (e.g., at a repetition rate of 3 GHz), while the envelope of this pulse train can be adjusted to use a 1.0-10 microsecond "macropulse" that can be delivered at a clinically useful repetition rate (e.g., 1.0 to 30 Hz or higher). These cited references have described a number of different types of light sources, and the stimulation parameters that may be used in different medical applications using both coherent and non-coherent light and may be relied upon by the present invention.

The light source may be a gas or non-gaseous light emitting source and can include a number of types of light-emitting diodes. Laser diodes produce a beam of light or radiation that is essentially monochromatic, is sharply collimated and is coherent. These diodes can provide light essential at one frequency (at a time, although they may be adjustable) with a small angle of divergence. Superluminous diodes provide light with decreased coherence compared to laser diodes, but this remains highly directional and is still limited in its frequency range. Semiconductor laser diodes have higher power outputs and narrower beam divergence and can also be utilized to provide treatment. All of these light sources may be included in the ferrule systems described herein. Stimulation may be used to provide photothermal, photochemical, and/or photomechanical effects on neural tissue.

Optical Sensing and Stimulating Operations

Optical stimulation may be used in the treatment of various neurological conditions, especially those which have already been shown to benefit from electrical stimulation. The stimulation subsystem 426 may be coupled to an optical SEST-module 436b and a fiber optic lead 438b, enabling optical stimulation of neural structures in the brain, spinal cord, and nerves. Generally, the stimulator of optical SEST-module 436b includes a controllable light emitter (such as at least one LED or laser diode) that is situated onboard, in close proximity to the device 1b, or is external to the patient, and the light is transmitted to the stimulation site via SEST conduit 61. By using a remote light source connected to optical fibers of the device 1b, the light source may be implanted in a location that is able to accommodate the volume of the device.

Eligible regions may be the pectoral region, abdominal cavity, or any other suitable region currently used with known implantable pulse generators.

One or more lenses may be used at the proximal or distal ends of the SEST conduit 61 to increase light collection from the emitter (at the proximal end) and to focus the optical stimulation (at the distal end). It should be understood that optical stimulation intensity is a function of both wavelength and intensity; different patients and different targets will react differently to different light colors, intensities, stimulation pulse widths, and stimulation burst durations (where pulse trains are delivered). The implantation of the optical probes may occur in a number of manners. The probes can be placed on the skull, but below the scalp, within the skull, under the skull, or on the ventral side of the ferrule as may occur using and SEST-grid. Light therapy may be performed in combination with pharmacologic intervention in order to increase the clinical efficacy of the drug treatment or decrease the necessary dose.

There are a number of advantages of using a SEST grid. For example, optical SEST probes located within subcortical tissue require ablation or adaptation of tissue to permit the residence of the physical dimensions of the probe. Regardless of the modality of stimulation or sensing, the SEST-grid elements may provide SEST functions for a larger area of the cortex than may occur with conduit based approaches, and allow for temporal-spatial and spatial patterns of sensed data (e.g., perfusion data) to be measured. Further, the optical elements of the SEST-grid may be angled to provide more accurate summation of the optical stimulation signals emitted from several sources compared to conduit based implementations. Further, optical stimulators of the SEST-grid may be programmably angled to provide changes to the stimulation angle, the area of stimulation, and the area of superposition since the hardware required for these features can be located above the grid and within the device 1b. Light stimuli may be shaped to produce 3-dimensional patterns. This may be accomplished through lenses and multiple beams that converge on a given location. This is difficult to do with optical fiber based techniques compared to the SEST-grid. Optical switching technologies on the grid permit the SEST elements to be stimulated in arbitrary patterns in space and time.

The optical data may be combined with data derived from other sensors located centrally or peripherally, such as EEG data or EKG data, in order to contextualize and sensibly analyze the incoming optical signals which may vary, for example, as a function of heartbeat or activity level. The characteristics of optical sensing which are accomplished by the optical grid, including those described in co-pending U.S. application Ser. No. 11/404,579, which is hereby incorporated by reference in its entirety. Because methods such as NIRS often use more than one wavelength (e.g., 775, 825, 850, and 904 nm), the SEST elements, including those of the SEST-grid, may be designed to also emit these other wavelengths. The light source may provide a plurality of light signals either simultaneously or at different times, and each of these signals may be transmitted from the source by at least one optical fiber to the optical SEST element. The routing of the signal may be controlled by the implantable device 1b.

The light source may provide at least coherent light or non-coherent light of at least one wavelength and can be any form of radiant energy sufficient to modulate (e.g., stimulate) activity in target tissues. The optical stimulation parameters may include at least one of: dose (duration×intensity), duration, intensity, frequency, modulation frequency, envelope type, pulse shape, inter-pulse interval, pulse duration, wavelength, wavelength variance, wavelength variance over time, power, monochromaticity (%), intensity of modulation with specific endogenous frequencies, overlap of simultaneously presented beams, angle of the light emitter, lens characteristics, aperture characteristics, all of which may be fixed or programmable. Optical stimulation may be used for both activation and inactivation of target tissue. For example, high frequency pulses may be used to inactivate neural tissue similar to high frequency electrical stimulation (where pulse repetition rate may be approximately above 500 Hz), although, similar to electrical stimulation, issues of heat must be taken into account. Neural modulation may also be possible such as hyperpolarization induced "freezing" of a neural population or modulation of the likelihood of firing when coupled with intrinsic input that concurrently excites the optically stimulated region. Light stimulus parameters may be used to selectively control which neural elements in the surrounding tissue are excited. The stimulus parameters may also control the spatial extent of neural elements which are excited. Stimulation frequencies using light stimulation may be substantially similar to those using electrical stimulation. Pulse widths may be substantially shorter.

In various applications, it is useful to provide spatial stimulation patterns using a number of SEST stimulation elements, which preferably exist on the SEST-grid. The multiple stimulation elements of the grid can be inserted adjacent to neural tissue so that each stimulation contact is in a different location. The amount, location, and timing of stimulation can be individually adjusted so that the greatest benefit of stimulation is obtained. The stimulation provided at any particular element, or by the set of elements, may be adjusted to minimize tissue damage with similar resultant stimulation or inhibition. The spatial summation of monochromatic light can occur when two light beams overlap in space and produce constructive interference (photometric summation) or when the spatial overlap is partial, or adjacent, where larger areas of tissue are simultaneously or consecutively stimulated.

Optical catheters typically deliver optical energy to the brain. The optical catheters are often realized using one or more optical fibers each of which stimulates only one or a small group of neurons. These fibers need to be carefully inserted into the tissue to be stimulated, oriented correctly, and may become less useful over time due to post-surgical migration of the optical leads. Utilizing an optical grid provides for a more stable application of stimulation. A feature of the invention is the provision of a SEST-grid for optical stimulation primarily to the cortex, the grid having a number of advantages such as the sustained superposition of light beams from sources which are stable in location and orientation over time compared to that provided by optical fibers. Unlike a spatial array formed from individual fibers that are positioned so that signal points are aligned in some manner, the optical SEST-grid does not rely upon the surgeon placing a series of fibers in exact locations with exact orientations in order to provide spatial stimulation with the accuracy of the grid.

In relation to the optical sciences, the following terms are generally understood to have the following meanings. "Light" refers to optical energy, or other types of electromagnetic radiation, having any wavelength (e.g., visible light or energy of longer and shorter wavelength, including laser, UV, and diode light). "Light source" refers to an optical signal generator for providing light over at least one specified range of wavelength, duration, and according to any arbitrary wave shape envelope (e.g., pulses), and may be implanted or external to the patient. "Light-stimulation point" (LSP) refers to a point from which light leaves the stimulation system so that it is conveyed to target tissue (e.g., the distal end of an implanted optical fiber or a stimulation pixel). "Optical conduit" refers to conduits that conduct light from one location to another (e.g., at least one optical fiber).

Additional Stimulation Systems and Methods

Chemicals may be delivered by the chemical delivery module in response to a signal from the control subsystem 432, which may be directed to do so by the external patient programmer 440. Chemical compounds useful for administration include, but are not limited to calcium chelators, chemotherapeutic agents, cytokines, genetic therapy agents, immunotherapeutic agents, ion channel blockers, ion channel activators, neuropeptides, neuroregulators such as neuromodulators and neurotransmitters, nutrients, receptor agonists, receptor antagonists, photoreactive/electroactive compounds, and combinations thereof. These chemical compounds may also include, mimic, or modulate a neurotransmitter such as dopamine, acetylcholine, glutamate, norepinephrine, epinephrine, histamine, serotonin, neuropeptides (such as cholecystokinin) and their precursors and metabolites (e.g., L-DOPA and DOPAC, respectively).

Chemical therapy may include drugs that are selected to be responsive to concurrent stimulation such as optical or thermal stimulation. The drug may be responsive to light energy with a specific wavelength, and the stimulation of the tissue produces localized therapy approximately within the field of the second modality of stimulation. When the drug is responsive to heat (or cold) the heat may be produced by electrical energy, thermal, or photonic energy. The non-drug stimulation modality may be delivered by a probe at the end of a stimulation conduit that includes a drug catheter.

Chemicals may be introduced into a patient by the device 1b or by an external device, or by a physician. For example, in the case of chemotherapy for brain tumors, chemotherapeutic agents can be delivered to the patient. An implanted device 1b as described herein may be used to provide therapy in conjunction with this chemotherapeutic treatment. For example, an implantable device may provide local drug delivery of a second drug to a specific brain target in conjunction with the systemic delivery of a first drug. Additionally, the implantable device may provide stimulation such as thermal, optical, sonic, vibratory, or electrical stimulation to an area of the brain in order to accomplish at least one of the following: activate drug in that same area, cause that area to increase in activity to concurrently increase uptake of the drug, or increase the permeability of the neural target in order to increase uptake of the drug. Further, the implantable device may be used to acutely increase the permeability of the blood brain barrier so that drugs provided systemically can pass through the blood brain barrier at a greater rate and amount than would occur in the absence of this neurostimulation. The neurostimulation can occur in an interval that is slightly prior to the systemic, or non-brain delivery of the drug, concurrent with the drug delivery, or after the drug delivery. The stimulation may be accomplished by one or more stimulators configured to stimulate different (or the same) neural targets, in order to alter the permeability of the blood brain barrier.

With respect to thermal regulation, brain cooling has been shown to be useful in the treatment of disorders such as epilepsy and excitotoxicity related to brain insult and stroke (Imoto H., Fujii M., Uchiyama J., Fujisawa H., Nakano K., Kunitsugu I., Nomura S., Saito T., Suzuki M. Use of a Peltier chip with a newly devised local brain-cooling system for neocortical seizures in the rat. Technical note. *J Neurosurg.* 2006 January, 104(1):150-6; Burton J. M., Peebles G. A., Binder D. K., Rothman S. M., Smyth M. D. Transcortical cooling inhibits hippocampal-kindled seizures in the rat. *Epilepsia.* 2005 December, 46(12):1881-7; Yenari M. A., Zhao H., Giffard R. G., Sobel R. A., Sapolsky R. M., Steinberg G. K. Gene therapy and hypothermia for stroke treatment. *Ann NY Acad Sci.* 2003 May, 993:54-68; discussion 79-81).

The implantable device of the current invention may provide a number of advantages when used in methods that apply cooling to the brain, such as cooling the cortical surface. When the removal of heat from neural tissues is achieved by an implanted neurostimulation device, the energy required will be a function of a number of variables including the heat-transfer characteristics of the cooling system and the distance over which the heat must travel prior to being removed. Rather than removing brain tissue in order to insert a probe that has enough surface area to be capable of heat transfer, or using a neurostimulation lead to transfer heat from one area to another, the incorporation of a cooling system into the ferrule system allows for a relatively large surface area to be used in the process of cooling. Further, the ferrule may act as an efficient means for removing heat from within the skull to outside of this structure. In one variation, a metallic flap is attached to the outside of the skull below the scalp in order to provide an increased surface area for heat transfer and dissipation. This utilizes the temperature differential between brain and scalp, which can serve to provide a natural gradient for energy transfer. Although only small changes in temperature have been shown to produce therapeutic benefit, the amount of energy needed for this process may be quite large in an implanted device, to the extent that this may be prohibitive. The use of a skull-mounted cooling system incorporated into the ferrule may overcome energy usage and heat transfer problems which are inherent other types of conventional implantable devices such as neurostimulators.

Peltier devices are commonly referred to as thermal chips, thermoelectric (TE) modules, or heat pumps and are usually small solid-state devices that move heat energy from a cold side to a hot side. The hot side, or "heat sink" is where heat accumulates, and this heat must be removed in order for the device to function efficiently. A skull-mounted implantable device is therefore well suited to serve this function and the cool side can be located intracranially, while the heat sink may be located extracranially. For example, the heat sink may be the top-side of the neural stimulator, or as shown in FIG. 2, the heat sink may be implemented by connecting the top surface of the implantable device to one or more metal flaps which may be attached to the dorsal section of the skull, beneath the scalp. Further, a liquid, which may be cooled at a remote location, may be circulated in order to draw heat away from the heat sink. Since the liquid does not enter the cranium, the risk of leakage into the brain in the case of a rupture in the device is minimized. Since the implantable device itself may produce, or be affected by, heat produced during the transfer process, the Peltier device and stimulation grid may be located on a separate ferrule from that which houses the implantable device and may have a communication link with the implantable device in order to be controlled.

Probes and methods of using these probes have been previously described in U.S. application Ser. No. 11/404,579, which is hereby incorporated by reference in its entirety, and include: electromagentic probes and methods of use, chemical probes and method of use, impedance probes and method of use, thermal probes and methods of use, and sonic probes and methods of use.

The sonic probe may also be realized as a sound transducer capable of emitting sound stimulation and even infrasound stimulation. The envelope of the sonic stimulation may be modulated using any arbitrary waveform, but other modulation including frequency modulation of the carrier, is also possible. The sonic probe may be realized as elements of the SEST-grid. Ultrasonic stimulation (e.g., via a piezoelectric transducer) may occur at frequencies greater than approximately 1 MHz and ultrasonic sensing can occur by receiving sound energy in a similar range of frequencies. Pulsed measurements enable selection of measurement depth (e.g., the distance in front of the probe 436d from which a measurement is taken). Regardless of the variation, when placing the sonic probes, it is particularly important to avoid gas bubbles and pockets in front of the transducer because such obstructions may confound both stimulation and sensing. Accordingly, when implemented in an SEST-grid, the grid should be snugly adjacent to the cortex if possible. Sonic stimulation has a number of uses, for example, ultrasonic stimulation generally operates to increase perfusion at the stimulation site and sonic stimulation can be used to disrupt emerging epileptiform activity.

With a sufficient number of electrodes disposed around a target site, it is possible to obtain a series of measurements (which may be between different sets of SEST-elements in impedance sensing) in order to reconstruct a tomographic image of, for example, blood flow using well known techniques. When realized within the SEST-grid, the tomographic data image which is derived may be of much better quality and resolution than data obtained from conventional conduit-based probes. In one variation, data is collected for tomographic measurements by the device 1b and is periodically transferred to the programmer 440 or other external apparatus, where the intensive computations needed to reconstruct visualizations or assess spatial patterns are more feasibly carried out. However, the SEST-grid data can also be evaluated by the device 1b itself in order to detect events meriting responsive stimulation.

Providing therapy is not restricted to the treatment of a diseased or abnormal condition, but also includes any function of the modulators, ferrules, and ferrule systems that produces desired results. Therapy applications include, but are not limited to: centrally mediated cardiac pacing, centrally mediated modulation of cardiac activity; spinal cord stimulation; reduction of inflammation; enhanced healing and perfusion; stimulation induced microcirculation; treatment of epileptic, movement, pain, psychiatric and mood disorders; deep brain stimulation; stroke and recovery from vascular disorders and insults; neurodegenerative disorders; aging disorders; disorders of eating, digestion, and voiding; sensory disorders; promotion of plasticity related to compensating for a deficit; and, cranial, sensory, vagus, and peripheral nerve stimulation. Further, tissue changes due to stimulation may include, but are not limited to, changes in the structure, function, activation level, activation threshold, responsiveness, biochemistry and/or metabolism of a viable tissue. Stimulation may include modulating tissue to promote excitation, inhibition, facilitation of endogenous activity or other type of desired modulation of a target tissue, as may be desired by the treatment program implemented by the ferrule system.

All publications, patents, and patent applications cited herein are hereby incorporated by reference in their entirety for all purposes to the same extent as if each individual publication, patent, or patent application were specifically and individually indicated to be so incorporated by reference. Although the foregoing ferrules, ferrule systems, and their methods of use have been described in some detail by way of illustration and example for purposes of clarity of understanding, it will be readily apparent to those of ordinary skill in the art, in light of the description herein provided, that certain changes and modifications may be made thereto without departing from the spirit and scope of the appended claims.

The invention claimed is:

1. An intracranial ferrule comprising:
a bottom portion having a dorsal surface and a ventral surface, and configured to be implanted in a cranium with the ventral surface being adjacent neural tissue,
a holding area attached to the bottom portion adjacent the dorsal surface for retaining an implantable device therein, and
one or more modulators disposed on the bottom portion, configured to be coupled to the implantable device while the holding area retains the implantable device therein, and configured to perform a function on the neural tissue adjacent the one or more modulators.

2. The intracranial ferrule of claim 1 wherein the one or more modulators comprise a sensing element configured to sense data from the neural tissue.

3. The intracranial ferrule of claim 2 wherein the sensed data is selected from the group consisting of EEG data, neuronal recordings, ultrasound and doppler shift ultrasound data, oximetry data, optical sensing data, blood pressure recordings, impedance measurements, measurements of blood gases or chemical composition, measurements of temperature and acceleration, measurements of emitted or absorbed radiation, and combinations thereof.

4. The intracranial ferrule of claim 2 wherein the sensing element comprises an optical sensor.

5. The intracranial ferrule of claim 2 wherein the sensing element comprises an electrical sensor.

6. The intracranial ferrule of claim 2 wherein the sensing element comprises a chemical sensor.

7. The intracranial ferrule of claim 2 wherein the sensing element comprises a thermal sensor.

8. The intracranial ferrule of claim 2 wherein the sensing element comprises a pressure sensor.

9. The intracranial ferrule of claim 2 wherein the sensing element comprises a sonic sensor.

10. The intracranial ferrule of claim 2 wherein the sensing element is configured to detect a neurological condition.

11. The intracranial ferrule of claim 1 wherein the one or more modulators comprise a stimulation element configured to stimulate the neural tissue.

12. The intracranial ferrule of claim 11 wherein the stimulation element comprises an optical stimulator.

13. The intracranial ferrule of claim 11 wherein the stimulation element comprises an electrical stimulator.

14. The intracranial ferrule of claim 11 wherein the stimulation element comprises a chemical stimulator.

15. The intracranial ferrule of claim 11 wherein the chemical stimulator is configured to deliver a therapeutic agent to the neural tissue.

16. The intracranial ferrule of claim 15 wherein the therapeutic agent is selected from the group consisting of calcium chelators, chemotherapeutic agents, cytokines, genetic therapy agents, immunotherapeutic agents, ion channel blockers, ion channel activators, neuropeptides, neuroregulators such as neuromodulators and neurotransmitters, nutrients, receptor agonists, receptor antagonists, photoreactive/electroactive compounds, and combinations thereof 17. The intracranial ferrule of claim 11 wherein the stimulation element comprises a thermal stimulator.

18. The intracranial ferrule of claim 17 wherein the thermal stimulator is configured to cool the neural tissue.

19. The intracranial ferrule of claim 17 wherein the thermal stimulator is configured to provide heat to the neural tissue.

20. The intracranial ferrule of claim 11 wherein the stimulation element comprises a pressure stimulator.

21. The intracranial ferrule of claim 11 wherein the stimulation element comprises a sonic stimulator.

22. The intracranial ferrule of claim 11 wherein the stimulation element is configured to treat a neurological condition.

23. The intracranial ferrule of claim 1 wherein the one or more modulators are configured as a grid on the dorsal surface.

24. The intracranial ferrule of claim 1 wherein the one or more modulators are configured as a grid on the ventral surface.

25. The intracranial ferrule of claim 1 further comprising a heat sink tab disposed on the holding area to be extracranially located if the bottom portion is disposed in a cranium.

26. The intracranial ferrule of claim 25 wherein the heat sink tab is connected to a skull-mounted heat sink.

27. The intracranial ferrule of claim 1 wherein the ferrule further comprises one or more connectors configured to reversibly attach the ferrule to the implantable device.

28. The intracranial ferrule of claim 1 wherein the implantable device comprises a neurostimulator.

29. The intracranial ferrule of claim 1 wherein a portion of the ferrule is configured to reversibly attach to a power supply.

30. The intracranial ferrule of claim 1 further comprising a conduit storage area.

31. The intracranial ferrule of claim 30 wherein the conduit storage area comprises at least one conduit anchor.

32. The intracranial ferrule of claim 1 further comprising a wall portion attached to and extending upwardly from the dorsal surface of the bottom portion and disposed around a portion of the holding area, and one or more cranial attachment tabs coupled to the wall portion and configured to secure the intracranial ferrule to a cranium in an orientation having the ventral surface of the bottom portion adjacent the neural tissue and to prevent movement of the ferrule while the implantable device is urged into the holding area and coupled to the ferrule or urged out of the holding area and decoupled from the ferrule.

33. A system for treating a neurological condition comprising:
an implantable device; and
an intracranial ferrule comprising a bottom portion having a dorsal surface and a ventral surface, and configured to be implanted in a cranium with the ventral surface being adjacent neural tissue, a holding area attached to the bottom portion adjacent the dorsal surface for retaining an implantable device therein, and one or more modulators disposed on the bottom portion, configured to be coupled to the implantable device while the holding area retains the implantable device therein, and configured to perform a function on the neural tissue adjacent the one or more modulators.

34. The system of claim 33 wherein the implantable device comprises a neurostimulator.

35. The system of claim 33 wherein the implantable device comprises one or more interface connectors configured to reversibly secure the implantable device to the ferrule.

36. The system of claim 33 wherein the implantable device comprises a control subsystem configured to coordinate sensing and stimulating functions of the ferrule.

37. The system of claim 33 wherein the ferrule comprises one or more retainer tabs for reversibly securing the implantable device within the ferrule.

38. The system of claim 33 wherein the one or more modulators comprise a sensing element configured to sense data from the neural tissue.

39. The system of claim 38 wherein the sensed data is selected from the group consisting of EEG data, neuronal recordings, ultrasound and doppler shift ultrasound data, oximetry data, optical sensing data, blood pressure recordings, impedance measurements, measurements of blood gases or chemical composition, measurements of temperature and acceleration, measurements of emitted or absorbed radiation, and combinations thereof.

40. The system of claim 38 wherein the sensing element comprises an optical sensor.

41. The system of claim 38 wherein the sensing element comprises an electrical sensor.

42. The system of claim 38 wherein the sensing element comprises a chemical sensor.

43. The system of claim 38 wherein the sensing element comprises a thermal sensor.

44. The system of claim 38 wherein the sensing element comprises a pressure sensor.

45. The system of claim 38 wherein the sensing element comprises a sonic sensor.

46. The system of claim 38 wherein the sensing element is configured to detect a neurological condition.

47. The system of claim 33 wherein the system further comprises one or more stimulation probes.

48. The system of claim 33 wherein the system further comprises one or more sensing probes.

49. The system of claim 33 wherein the one or more modulators comprise a stimulation element configured to stimulate the neural tissue.

50. The system of claim 49 wherein the stimulation element comprises an optical stimulator.

51. The system of claim 49 wherein the stimulation element comprises an electrical stimulator.

52. The system of claim 49 wherein the stimulation element comprises a chemical stimulator.

53. The system of claim 52 wherein the chemical stimulator is configured to deliver a therapeutic agent to the neural tissue.

54. The system of claim 53 wherein the therapeutic agent is selected from the group consisting of calcium chelators, chemotherapeutic agents, cytokines, genetic therapy agents, immunotherapeutic agents, ion channel blockers, ion channel activators, neuropeptides, neuroregulators such as neuromodulators and neurotransmitters, nutrients, receptor agonists, receptor antagonists, photoreactive/electroactive compounds, and combinations thereof.

55. The system of claim 49 wherein the stimulation element comprises a thermal stimulator.

56. The system of claim 55 wherein the thermal stimulator is configured to cool the neural tissue.

57. The system of claim 55 wherein the thermal stimulator is configured to provide heat to the neural tissue.

58. The system of claim 49 wherein the stimulation element comprises a pressure stimulator.

59. The system of claim 49 wherein the stimulation element comprises a sonic stimulator.

60. The system of claim 33 wherein the one or more modulators are configured as a grid on the dorsal surface of the bottom portion.

61. The system of claim 33 wherein the one or more modulators are configured as a grid on the ventral surface of the bottom portion.

* * * * *